United States Patent [19]

D'Halluin et al.

[11] Patent Number: 5,641,664
[45] Date of Patent: Jun. 24, 1997

[54] PROCESS FOR TRANSFORMING MONOCOTYLEDONOUS PLANTS

[75] Inventors: Kathleen D'Halluin, Mariakerke; Elke Gobel, Ghent, both of Belgium

[73] Assignee: Plant Genetic Systems, N.V., Brussels, Belgium

[21] Appl. No.: 64,121

[22] PCT Filed: Nov. 21, 1991

[86] PCT No.: PCT/EP91/02198

§ 371 Date: Jun. 23, 1993

§ 102(e) Date: Jun. 23, 1993

[87] PCT Pub. No.: WO92/09696

PCT Pub. Date: Jun. 11, 1992

[30] Foreign Application Priority Data

Nov. 23, 1990 [EP] European Pat. Off. ............. 90403332
Jul. 8, 1991 [EP] European Pat. Off. ............. 91401888

[51] Int. Cl.$^6$ ............................. A01H 1/00; A01H 4/00; A01H 5/00; C12N 5/04; C12N 5/14; C12N 15/00
[52] U.S. Cl. ............... 435/172.3; 435/69.1; 435/252.2; 800/200; 800/205; 800/DIG. 56; 935/52; 935/67
[58] Field of Search ..................... 800/200, 205, 800/250, DIG. 56; 435/172.1, 172.3, 240.1, 240.4, 240.48, 240.49, 240.5, 69.1, 252.2; 935/52, 53, 67

[56] References Cited

U.S. PATENT DOCUMENTS 5,187,073  2/1993  Goldman et al. ............. 435/172.3

FOREIGN PATENT DOCUMENTS 0 203 790   12/1986  European Pat. Off. .
0 334 539    9/1989  European Pat. Off. .
0 334 029   11/1989  European Pat. Off. .
37 38 874   11/1988  Germany .
40 13 099   10/1991  Germany .
8801444      1/1990  Netherlands .
88/09374    12/1988  WIPO .
WO91/10725   7/1991  WIPO .
WO92/12250   7/1992  WIPO .

OTHER PUBLICATIONS

*The Plant Cell*, Rudy A. Dekeyser, et al., "Transient Gene Expression in Intact and Organized Rice Tissues", vol. 2, pp. 519–602, Jul. 1990.
Abstract of German Patent No. DE 4013099.
Abstract of Netherlands Patent No. NL 8801444.
Abstract of German Patent No. DE 3717301.
Abstract of German Patent No. DE 3738874.
Chibbar et al. Mar. 31–Apr. 22, 1990. Journal of Cellular Biochemistry. Supplement 14E, 1990.

*Primary Examiner*—Erich E. Veitenheimer
*Attorney, Agent, or Firm*—Burns, Doane, Swecker & Mathis, LLP

[57] ABSTRACT

A rapid and efficient method for transforming monocotyledonous plants, especially gramineous plants, particularly corn, using either intact tissue capable of forming compact embryogenic callus or compact embryogenic callus obtained from such tissue to obtain transgenic monocotyledonous plants, is provided. Preferably, the tissue or embryogenic callus is wounded and/or degraded prior to transformation. The resulting wounded and/or degraded, intact tissue or compact embryogenic callus is then transformed, preferably by direct gene transfer, e.g., by means of electroporation, with one or more DNA fragments (e.g., foreign DNA fragments).

32 Claims, 4 Drawing Sheets

PROCESS FOR TRANSFORMING MONOCOTYLEDONOUS PLANTS

This invention relates to a rapid and efficient method for transforming monocotyledonous plants generally, especially gramineous plants, particularly corn and other major cereals. The invention particularly relates to the use of either intact tissue capable of forming compact embryogenic callus or compact embryogenic callus obtained from such tissue to obtain transgenic monocotyledonous plants.

This invention also relates to novel transgenic gramineous plants, particularly cereals, which can be obtained by the transformation method of this invention.

BACKGROUND OF THE INVENTION

In recent years, there has been a tremendous expansion of the capabilities for the genetic engineering of plants. Many transgenic dicotyledonous plant species have been obtained. However, many species of plants, especially those belonging to the Monocotyledonae and particularly the Gramineae, including economically important species such as corn, wheat and rice, have proved to be very recalcitrant to stable genetic transformation.

Difficulties have been encountered in achieving both: a) integrative transformation of monocot plant cells with DNA (i.e., the stable insertion of DNA into the nuclear genome of the monocot plant cells) and b) regeneration from transformed cells of phenotypically normal monocot plants, such as phenotypically normal, fertile adult monocot plants. It has been suggested that such difficulties have been predominantly due to the nonavailability of monocot cells that are competent with respect to: 1) DNA uptake, 2) integrative transformation with the taken-up DNA, and 3) regeneration of phenotypically normal, monocot plants from the transformed cells (Potrykus (1990) Bio/Technology 9:535). In general, direct gene transfer into protoplasts (using polyethyleneglycol treatment and/or electroporation) has seemed to have the best potential for success. Protoplasts for use in such direct gene transfer methods have most often been obtained from embryogenic cell suspension cultures (Lazzeri and Lörz (1988) Advances in Cell Culture, Vol.6, Academic press, p. 291; Ozias-Akins and Lörz (1984) Trends in Biotechnology 2:119). However, the success of such methods has been limited due to the fact that regeneration of phenotypically normal plants from protoplasts has been difficult to achieve for most genotypes.

Recently, success has been reported in the transformation of, and regeneration of phenotypically normal plants from, certain lines of rice (Shimamoto et al (1989) Nature 338:274; Datta et al (1990) Bio/Technology 8:736; and Hayashimoto et al (1990) Plant Physiol. 93:857) and corn (Gordon-Kamm et al (1990) Bio/Technology 2:603; Fromm et al (1990) Bio/Technology 8:833; Gould et al (1991) Plant Physiology 95:426; and PCT publications WO91/02071 and WO89/12102). However, it is not clear from such reports that their processes of transformation and regeneration are applicable to monocots generally, particularly gramineous plants, quite particularly cereals.

SUMMARY OF THE INVENTION

This invention provides a novel method for efficiently and reproducibly transforming the genome of a monocotyledonous plant, particularly a gramineous plant such as a major cereal (e.g., corn, wheat, rice, rye, etc). This method comprises the transformation with DNA of cells of either: a) an intact tissue of the monocotyledonous plant, which tissue is capable of forming compact embryogenic callus or b) a compact embryogenic callus, particularly its embryogenic sectors, obtained from such intact tissue, such cells being competent with respect to: 1) uptake of the DNA, 2) integrative transformation of the plant genome, preferably its nuclear genome, with the DNA and 3) regeneration of the phenotypically normal plant (e.g., phenotypically normal, fertile adult plant) from the cells following the transformation of their genome. Such competent cells are preferably obtained by wounding and/or degrading the intact tissue or the compact embryogenic callus of the plant, for example by: a) cutting either the intact tissue and the cells thereof or the compact embryogenic callus and the cells thereof obtained from such intact tissue; and/or b) depending upon the nature of the intact tissue or the compact embryogenic callus, treating the intact tissue or the compact embryogenic callus with an enzyme to degrade the cell walls of the intact tissue or compact embryogenic callus.

The resulting wounded and/or degraded, intact tissue or compact embryogenic callus, containing the competent cells of this invention, can be transformed, preferably by direct gene transfer, such as by means of electroporation, with one or more DNA fragments (e.g., foreign DNA fragments), preferably linear DNA fragments. Preferably, at least one of the DNA fragments contains a gene which can serve as a selectable or a screenable marker, preferably a selectable marker, for transformed plant cells. Such a marker DNA fragment can be located on the same DNA fragment or on a separate DNA fragment as another gene or other gene(s) of interest.

The transformed cells can be separated in a conventional manner from non-transformed cells by culturing on a selective medium, preferably for a prolonged time, and the transformed cells, thus selected, can be regenerated in a conventional manner into phenotypically normal plants (e.g., mature plants) which possess the gene(s) of interest stably integrated in their genomes, particularly their nuclear genomes.

This invention also provides: novel competent cells of monocot plants, especially gramineous plants, particularly cereal plants, the genomes of which have been stably transformed with one or more DNA fragments; cell cultures consisting of such transformed cells; phenotypically normal plants (e.g., phenotypically normal, fertile plants) regenerated from such transformed cells; and seeds of such transformed plants. Among such transformed cells, cell cultures, plants and seeds are those transformed with a DNA fragment containing a gene that encodes a protein capable of killing or disabling a plant cell in which the protein is expressed and that is under the control of the tapetum-specific PTA29 promoter whereby the plants are male sterile. The transformed gramineous plants of this invention, particularly transformed corn and rice, are characterized by their being from plant lines, from which it is practically impossible with conventional techniques to regenerate the transformed plants, as phenotypically normal plants, from transformed embryogenic suspension cultures or from transformed protoplasts, particularly where for every 10,000 untransformed protoplasts of such plant lines, no more than about 500, especially no more than about 100, particularly no more than about 10, quite particularly no more than about 1, phenotypically normal plant(s) can be regenerated.

Lanes:
1: PstI digested DNA of phage lambda + HindIII digested pTTM1 (positive control—probe should hybridizes to 2824 bp pTTM1 fragment)
2: BglII digested genomic DNA
3: EcoRI digested genomic DNA
4: EcoRV digested genomic DNA
5: HindIII digested genomic DNA
6: BamHI digested genomic DNA
7: PvuI digested genomic DNA
8: PvuII digested genomic DNA
9: PstI digested genomic DNA
10: EcoRI digested plant genomic DNA of untransformed H99 plant (negative control)

Figure 3:
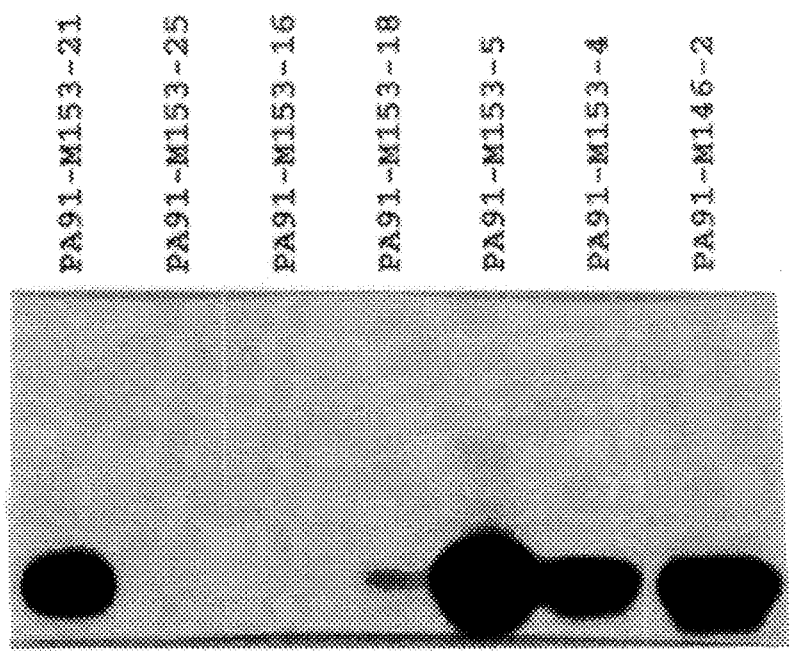

FIG. 3: NptII gel assays of Example 4 of seven transformants obtained by electroporation of compact embryogenic callus fragments derived from immature zygotic embryos.

Figure 4:
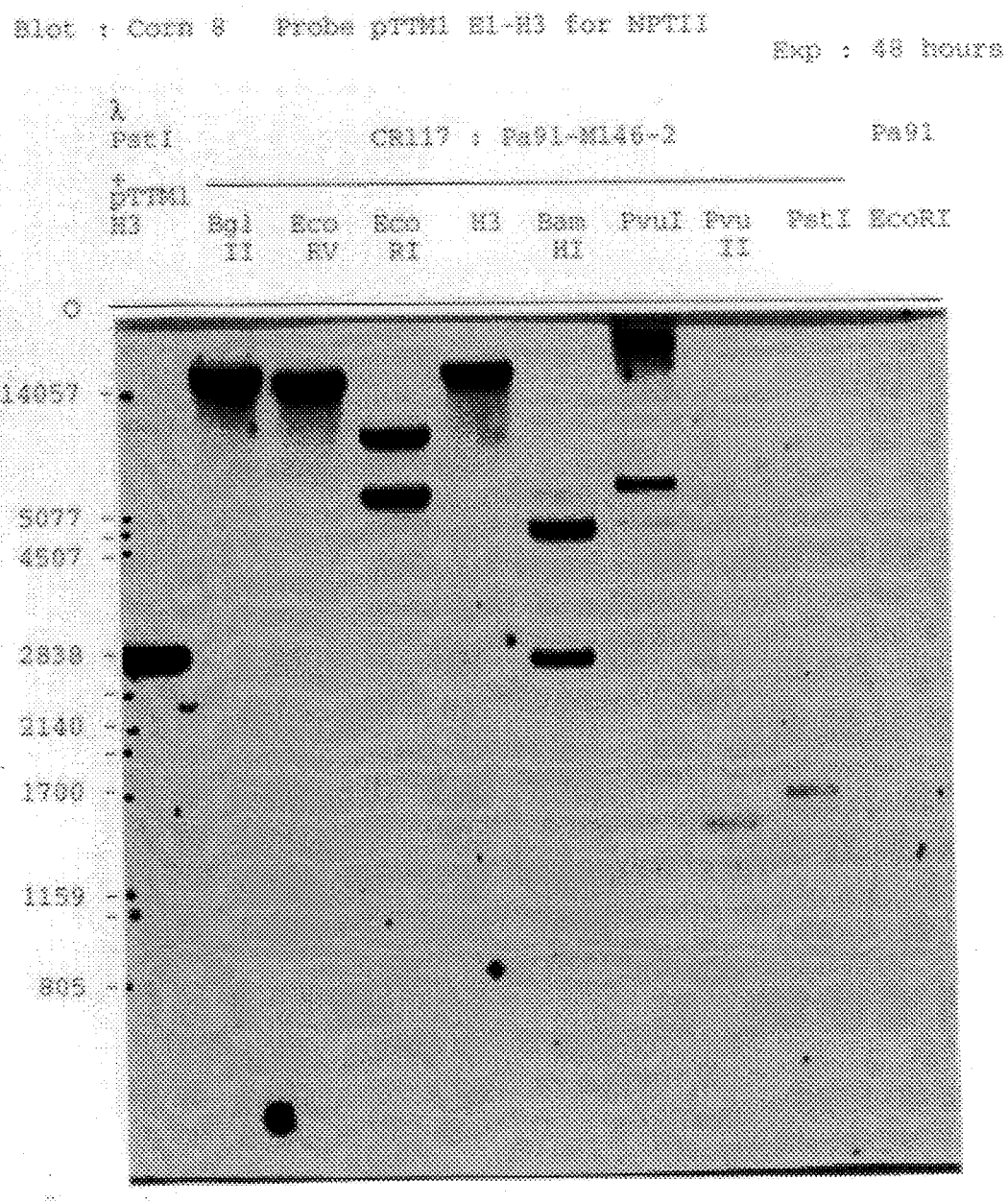

FIG. 4: Southern blots of Example 4 of genomic DNA of one of the corn transformants of Example 3 (Pa91-M146-2) using the sequence listed as Seq. Id. 2 as a probe. Lengths of standard fragments are indicated. The origin is indicated by 0.

Lanes:
1: PstI digested DNA of phage lambda + HindIII digested pTTM1 (positive control—probe should hybridizes to 2824 bp pTTM1 fragment)
2: BglII digested genomic DNA
3: EcoRI digested genomic DNA
4: EcoRV digested genomic DNA
5: HindIII digested genomic DNA
6: BamHI digested genomic DNA
7: PvuI digested genomic DNA
8: PvuII digested genomic DNA
9: PstI digested genomic DNA
10: EcoRI digested plant genomic DNA (negative control)

SEQUENCE LISTING

Seq. Id. No. 1: sequence of pDE108

Seq. Id. No. 2: sequence of probe used to detect chimaeric neo gene in Southern hybridizations Seq. Id. No. 3: sequence of a DNA fragment of plasmid pTTM8 used in the construction of plasmids pVE107 and pVE108 and comprising the promoter from the TA29 gene of tobacco and the barnase gene Seq. Id. No. 4: sequence of pDE110

DETAILED DESCRIPTION OF THE INVENTION

In monocots, embryogenic callus can be of two distinct and well known types (see: Vasil (1988) Bio/Technology 6:397; Armstrong and Green (1988) Crop Sci. 28:363). One type of embryogenic callus can best be described as compact and/or nodular and can often be considered as organized. Such callus, termed herein "compact embryogenic callus", is used in accordance with this invention. The other and generally less frequently occurring type of embryogenic callus can best be described as soft, friable and highly embryogenic, and such callus, termed herein "friable embryogenic callus", generally grows faster than the compact embryogenic callus. From either type of callus, phenotypically normal plants can be regenerated, and in both types of callus, somatic embryos are present in different stages of development. The appearance and final morphology of the two types of callus can differ in different monocot species, particularly in different cereal species. Nevertheless, the two types of callus can be readily distinguished from one another by persons skilled in the art of forming and manipulating tissue cultures of different monocot species.

In corn, compact embryogenic callus and friable embryogenic callus are more familiarly known as type I callus and type II callus, respectively. Various distinguishing features in the structure and properties of type I and type II corn calli are described in publications, such as: Armstrong and Phillips (1988) Crop Sci. 28:363; Springer et al (1979) Protoplasma 101:269; Fransz (1988) "Cytodifferentiation during callus initiation and somatic embryogenesis in Zea mays L.", Ph.D. Thesis, University of Wageningen, The Netherlands; Ozias-Akins et al (1982) Protoplasma 110:95; Novak et al (1983) Maydica 28:381; Ho et al (1983) Protoplasma 118:169; Green et al (1975) Crop Sci. 15:417; Freeling et al (1976) Maydica 21:97; Lu et al (1982) Theor. Appl. Genet. 62:109; Vasil et al (1985) Protoplasma 127:1; Dunstan et al (1978) Protoplasma 97:251; Vasil et al (1982) Bot. Gaz. 143:454; Green (1983) In: Basic biology of new developments in biotechnology, Hollaender et al (eds) Plenum Press, New York, pp. 195–209; Vasil et al (1984) Am. J. Bot. 71:158; and Kamo et al (1985) Bot. Gaz. 146:327.

Type I corn callus is essentially white, pale white or yellowish and compact in appearance, often has a nodular surface, and represents the generation and propagation of an organized set of tissues which is reflected in its nodular appearance. It is characterized by a high degree of cellular association and differentiation and by various structures, such as roots, leafy structures and vascular elements. Somatic embryos can generally be recognized. The origin of regenerated shoots is not always obvious and can apparently occur by both somatic embryogenesis and organogenesis. During somatic embryo development, embryoids can fuse and give rise to hard, white callus or can develop into secondary somatic embryos.

Type II corn callus is essentially soft, friable, white or pale-yellow, somewhat transparent in appearance and highly embryogenic. It grows rapidly and contains no vascular elements. Type II callus differs from non-embryogenic friable callus in containing numerous smooth and globular embryoids that may possess a suspensor-like structure by which the embryoids are attached to the callus. The embryoids can develop into well-organized somatic embryos.

Approximately the same distinguishing features, that are found in the two types of corn calli, can be used to distinguish between the compact embryogenic callus and the friable embyogenic callus of other monocot species, particularly cereal species such as rice (Kyozuka et al (1988) Theor. Appl. Genet. 76:887), wheat (Redway et al (1990) Theor. Appl. Genet. 76:609; Redway et al (1990) Plant Cell Reports 8:714), and barley.

From monocotyledonous plants generally, the compact embryogenic callus of this invention can be obtained by in vitro culture of explant sources such as immature zygotic embryos, mature seeds, leaf bases, anthers, microspores, young inflorescences, etc. In corn, the type I callus is most efficiently generated from immature zygotic embryos. The compact embryogenic callus can be induced from the appropriate explants and maintained in culture according to well-established methods (see Hodges et al (1986) Bio/Technology 4:219). During maintenance of the callus culture, care has to be taken to select and subculture only the embryogenic sectors of the calli in which are the embryogenic cells. Such cells can generally be characterized as small, tightly packed, thin-walled, richly cytoplasmic, highly basophilic cells containing many small vacuoles, lipid droplets and starch grains (Vasil (1988) supra). The most convenient way to remove, from a plant, tissues that are known to be capable of forming the compact embryogenic callus is by means of dissection.

The competent cells of this invention can be obtained directly from a monocotyledonous plant by cutting from the plant, in a conventional manner, intact tissue that is capable of forming compact embryogenic callus. The cells of such wounded intact tissue can then be stably transformed. However, it is preferred that such wounded intact tissue be cut into smaller fragments to wound further such tissue and provide more competent cells for transformation. The average maximum dimension of the tissue fragments is preferably 0.1 to 5 mm long, particularly 1 to 2.5 mm long, more particularly 1.25 to 1.75 mm long. In this respect, the wounded intact tissue of this invention can be any piece of tissue that is cut from the plant or any fragments thereof (e.g., cut pieces). Thus, the term "intact tissue" should be understood as referring to aggregates of monocot plant cells that are obtained from a naturally occurring plant part, without a tissue-culturing stage in between.

It is believed that the mechanical disruption or wounding of the intact tissue and its individual cells, by cutting the intact tissue from the plant and possibly further cutting it so as to disrupt or wound it further, is generally sufficient to generate the competent cells of this invention. In this regard, the terms "mechanical disruption" and "wounding" are intended to encompass the significant damaging of the cell wall of one or more cells of the intact tissue in order to expose the cell(s) and render the cell(s) open to insertion of a DNA fragment in accordance with this invention. Thus, "mechanical disruption" or "wounding" in accordance with this invention is not limited to cutting the cell wall but includes other methods of physically removing one or more portions of the cell wall or rendering the cell wall discontinuous in one or more places, such as by abrading, squeezing or striking the cell wall.

However, the mechanical disruption or wounding of the intact tissue in accordance with this invention can be supplemented or even replaced by a treatment of the intact tissue with an enzyme or enzyme mixture to degrade the plant cell walls, especially when the intact tissue is relatively large. The enzyme treatment can be carried out in a conventional manner. Preferably, the enzyme is applied to the intact tissue primarily to generate pores in its cell walls. It is therefore preferred that the enzyme treatment be relatively short (e.g., from 1 to 10 minutes depending upon the nature and the consistency of the intact tissue) so as not to cause a complete disruption of the tissue. Depending upon the type of plant, various enzymes or enzyme solutions can be used such as those listed by Powell and Chapman (1985) "Plant Cell Culture, A Practical Approach", R. A. Dixon ed., Chapter 3.

When the intact tissue, obtainable from the plant, is too small to be wounded (e.g., cut) or wounded intact tissue is too small to be further wounded (e.g., cut into smaller pieces), the enzyme treatment can be used to generate additional competent cells. Such an enzyme treatment can also be particularly useful, by itself, for forming competent cells of this invention in embryos, particularly in immature zygotic embryos isolated from developing seeds and in mature zygotic embryos isolated from mature (e.g., dry) seeds of, for example, corn. Embryos are generally not cut to remove them from seeds and generally cannot be cut into significantly smaller fragments without destroying their ability to generate compact embryogenic callus. Immature embryos are particularly important in corn as they are the only convenient and reliable source of compact embryogenic callus. In rice and other monocots, mature embryos can also be used. In this regard, for plants such as corn, it is preferred that the intact tissue (e.g., immature corn embryos) have a maximum length of about 0.5 to 2 mm, preferably 0.5 to 1.5 mm, even though smaller lengths of 0.5 to 1 mm can be used.

In accordance with this invention, the intact tissue is also preferably subjected to a period of, for example, about 15 minutes or more, preferably about 30 minutes to about 5 hours, particularly 2 to 3 hours, of preplasmolysis which involves placing the tissue in a conventional hypertonic solution, such as the electroporation buffer discussed below. The purpose of this preplasmolysis treatment is to separate at least partly, in the cells of the intact tissue, their protoplasts, preferably all or at least part of their cell membranes, from their cell walls. Such preplasmolysis is preferably carried out after any wounding of the intact tissue but before any enzyme treatment of the intact tissue. When the intact tissue has already been degraded by an enzyme treatment, it is preferred that any subsequent preplasmolysis be only for a brief period, and after the enzyme treatment of immature embryos of corn, as discussed above, it is preferred that such preplasmolysis not be carried out at all.

The competent cells of this invention can also be obtained by: culturing in vitro the intact tissue of this invention to produce compact embryogenic callus; and then cutting the callus into smaller fragments. The resulting callus fragments should comprise, wholly or at least in part, the embryogenic sectors or parts of the callus. The callus fragments also preferably have an average maximum length of 0.5 to 2.5 mm, particularly 1 to 2 mm, more particularly 1.25 to 1.75 mm, and preferably have a minimum length of about 0.1 mm. To obtain sufficient amounts of compact embryogenic callus, it is preferred to propagate the primary callus, as obtained from tissue explants, for at least one month and to subculture the embryogenic sectors of such primary callus at least once during this period. It is believed that the mechanical disruption or wounding of the embryogenic sectors of the compact embryogenic callus and their cells by, for example, cutting them is generally sufficient to generate the competent cells of this invention. However, the mechanical disruption of the callus may be supplemented or replaced by an enzyme treatment to degrade the callus cell walls, especially when the compact embryogenic callus fragments remain relatively large. This enzyme treatment can be carried out in a conventional manner. The enzyme treatment preferably serves primarily to generate pores in the cell walls of the cells of the callus fragments, and it is therefore recommended that the enzyme treatment be relatively short, preferably from 1 to 10 minutes depending upon the consistency of the callus fragments, so as not to cause a complete disruption of the tissues. Depending upon the monocot plant, various enzymes or enzyme solutions can be used such as those listed by Powell and Chapman (1985) supra. Preferably, the compact embryogenic callus fragments are also subjected to a period (e.g., 2 to 3 hours) of preplasmolysis, as discussed above.

The wounded and/or degraded, intact tissue or compact embryogenic callus fragments, particularly their embryogenic sectors, obtained as described above, are then brought into contact with one or more DNA fragments containing gene(s) of interest in order to transform their competent monocot plant cells of this invention. It is preferred that at least one of the genes of interest be adapted to serve as a selectable marker in the resulting transformed monocot plant cells. It is believed that direct gene transfer, particularly electroporation, provides optimal transformation efficiency. However, other known DNA transfer techniques can be used such as direct gene transfer using polyethyleneglycol, bombardment with DNA-coated microprojectiles (i.e., biolistic transformation using, for example, a particle gun), and Agrobacterium-mediated transformation.

The compact embryogenic callus, used in carrying out the plant transformation method of this invention, can have certain characteristics of a friable embryogenic callus. In this regard, a compact embryogenic callus or a friable embryogenic callus can change or be caused to change into a type of callus that has some of the characteristics of compact embryogenic callus as well as some characteristics of friable embryogenic callus. As a result, such an intermediate type of callus and embryogenic portions thereof can sometimes be transformed in accordance with this invention. Indeed, somatic embryos that develop on such an intermediate type of callus, as well as on friable embryogenic callus, can be isolated and can be wounded and/or degraded and then transformed as described above. Thus, in carrying out the method of this invention, such somatic embryos obtained from an intermediate type callus or a friable embryogenic callus can be regarded as equivalent to immature or mature zygotic embryos obtained from developing or mature seeds, particularly when electroporation is used as the means for transforming cells of the somatic embryos.

In accordance with this invention, electroporation can be carried out in a conventional manner. In this regard, the wounded and/or degraded intact tissue or callus fragments, particularly meristematic or embryogenic sections thereof, quite particularly embryogenic sections thereof, can be transferred to a cuvette suitable for use in an electroporation apparatus (e.g., as described by Dekeyser et al (1990) The Plant Cell 2:591). Preferably, about 10 to 500 mg, particularly about 50 to 200 mg, most particularly about 100 to 150 mg, of intact tissue or callus fragments per 200 µl of electroporation buffer are transferred to the cuvette. For cereals, such as corn, (where it is preferred to use intact enzyme-treated immature embryos), it is preferred that about 10 to 500 embryos, particularly about 50 to 150 embryos, more particularly about 75 to 125 embryos, in 200 µl of electroporation buffer are transferred to the cuvette. The DNA is then added to the cuvette, and the electroporation is carried out. Preferably, the DNA is coincubated (e.g., for about 1 hour) with the intact tissue or callus fragments prior to electroporation. It is believed that best results can be obtained with linear, rather than circular, DNA of relatively small size, preferably smaller than about 20 kb, especially smaller than 15 kb, particularly smaller than 10 kb, quite particularly smaller than 6 kb (e.g., down to about 2–3 kb). In this regard, multiple linear DNA fragments of different composition can be used to transform the competent cells of this invention with multiple genes of interests. Preferably, about 5 to 30 µg, particularly about 10–25 µg, quite particularly about 20 µg, of DNA is added to the cuvette containing the intact tissue or callus fragments. Particular electroporation conditions are not believed to be critical, and good results can be obtained, for example, with a discharge of one pulse with a field strength of 375 V/cm from a 900 µF capacitor using an electroporation buffer containing 150 mM NaCl or 80 mM KCl (Dekeyser et al (1990) supra).

When the transformation (e.g., by electroporation) is completed, the intact tissue or callus fragments, containing the transformed monocot cells, are transferred to a suitable culture medium, preferably a selective medium when the transformed cells contain a selectable marker. This transfer should be as soon as possible after, preferably immediately after, the transformation event and especially within one to three days after the transformation event. Preferably, the intact tissue or callus fragments transformed with a selectable marker are cultured using conventional culture conditions and culture media (see, e.g., references in Vasil (1988) supra) supplemented with a selective agent. The selection of the selective agent will depend on the selectable marker used in the DNA fragments to transform the cells of the intact tissue or callus fragments, as discussed below. The concentration of the selective agent should provide a very high selective pressure on the transformed cells so that only stable transformants, in which the DNA fragments containing the selectable marker are integrated, preferably fully integrated, in the genome of the cells, survive and can be isolated. Although such transformed intact tissue or callus fragments can be cultured for a few days on non-selective medium, it is preferred that they be transferred to selective medium as soon as possible and maintained for a prolonged period (e.g., as long as six months), preferably at least one month, especially two to three months, to produce significant amounts of transformed morphogenic callus, such as transformed compact embryogenic callus, which can be used to regenerate a phenotypically normal plant. It is also preferred that the hypertonicity of the medium be maintained for a limited time (e.g., up to two to three weeks), for instance by supplementing the medium with mannitol.

In accordance with this invention, any DNA fragment can be integrated in the genome, particularly the nuclear genome, of a monocotyledonous plant. Generally, the DNA fragment contains a foreign or endogenous gene or other DNA sequence which is functional in the transformed plant cells and confers an additional property to such cells and to plants regenerated from the cells. To this end, the DNA fragment preferably comprises one or more chimaeric genes which contain the following operably linked DNA sequences: 1) a promoter sequence capable of directing expression of a coding sequence in the plant cell (a "promoter"); 2) a sequence (a "coding sequence") coding for a protein with a specific activity within the plant cell (a "protein of interest"): and 3) suitable 3' transcription regulation signals. In order to obtain the required functionality of the protein, it may also be necessary that the protein be targeted to one or more particular compartments of the plant cell, such as the cytosol, mitochondria, chloroplasts or endoplasmatic reticulum. For targeting to the cytosol, the chimaeric gene, as described above, can be used as such. However for targeting to the other compartments, it is required that there be an additional sequence (a "targeting sequence") between the DNA fragments 1) and 2) of the chimaeric gene. If required, the chimaeric gene can also contain transcriptional and/or translational enhancers, and the codon usage of the DNA sequences can be optimized for expression in plant cells.

Chimaeric genes in accordance with this invention can be constructed according to well-established principles and techniques. In this regard, the various DNA sequences should be linked so that translation is initiated at the initiation codon of the coding sequence of the protein (or of the targeting sequence when it is present).

It is believed that the various constitutive and organ- and tissue-specific promoters that are presently used to direct expression of genes in transformed dicotyledonous plants will also be suitable for use in transformed monocots of this invention. In this regard, particular plant cells can be transformed with a chimaeric gene comprising: a coding sequence encoding a protein of interest; and upstream (i.e., 5') thereof, either a foreign or an endogenous promoter suitable for expression of the coding sequence. Suitable foreign constitutive promoters include: the promoter of the Cauliflower Mosaic Virus ("CaMV") isolates CM1841 (Gardner et al (1981) Nucl. Acids. Res. 9:2871) and CabbB-S (Franck et al (1980) Cell, 21:285) (the "35S promoter") which directs constitutive expression of heterologous genes (Odell et al (1983) Nature 313:810); a related promoter (the "35S3 promoter") which can be isolated from the CaMV isolate CabbB-JI (Hull and Howell (1978) Virology 86:482) and which differs from the 35S promoter in its sequence (the sequence of the 35S3 promoter is disclosed in European patent publication ("EP") 359617) and in its greater activity in transgenic plants (Harpster et al (1988) Mol. Gen. Genet. 212:182); and the TR1' and the TR2' promoters which drive the expression of the 1' and 2' genes, respectively, of the T-DNA of Agrobacterium (Velten et al (1984) EMBO J. 3:2723) and are wound-induced promoters. Suitable organ-specific, tissue-specific and/or inducible foreign promoters are also known (see, e.g., references cited in Kuhlemeier et al (1987) Ann. Rev. Plant Physiol. 38:221) such as the promoters of the small subunit genes (such as the 1A gene) of 1,5-ribulose bisphosphate carboxylase of *Arabidopsis thaliana* (the "ssu" promoter) which are light inducible promoters (Krebbers et al (1988) Plant Mol. Biol. 11:745) active only in photosynthetic tissue; the anther-specific promoters disclosed in EP 344029; and the seed-specific promoters of, for example, *Arabidopsis thaliana* (Krebbers et al (1988) Plant Physiol. 87:859). Promoters of particular usefulness for transforming monocots to render them male-sterile, as described in EP 344029, are the tapetum-specific promoters PTA29, PTA26 and PTA13, particularly PTA29, of EP 344029.

Likewise, it is believed that known 3' transcription regulation sequences and polyadenylation signals used in transformed dicotyledonous plants can be used in transformed monocots of this invention. Such 3' transcription regulation signals can be provided downstream (i.e. 3') of the coding sequence. In this regard, a particular plant cell can be transformed with a chimaeric gene containing either foreign or endogenous transcription termination and polyadenylation signals suitable for obtaining expression of the chimaeric gene. For example, the foreign 3' untranslated ends of genes, such as gene 7 (Velten and Schell (1985) Nucl. Acids Res. 13:6998), the octopine synthase gene (Gielen et al (1983) EMBO J. 3:835) and the nopaline synthase gene of the T-DNA region of *Agrobacterium tumefaciens* Ti-plasmid can be used.

For construction Of a chimaeric gene which can be expressed in a transformed plant cell, preferably in its cytoplasm followed by translocation of its protein of interest to the cell's mitochondria, chloroplasts and/or lumen of the endoplasmatic reticulum, suitable targeting sequences are known. Selection of such targeting sequences is not believed to be critical, and a particular plant cell can be transformed with a chimaeric gene containing either a foreign or endogenous targeting sequence encoding a targeting peptide which will provide translocation of the expression product of the gene. By "targeting peptide" is meant a polypeptide fragment which is normally associated, in an eucaryotic cell, with a chloroplast or mitochondrial protein or subunit of the protein or with a protein translocated to the endoplasmatic reticulum and which is produced in a call as part of precursor protein encoded by the nuclear DNA of the cell. The targeting peptide is responsible for the translocation process of the nuclear-encoded chloroplast or mitochondrial protein or subunit into the chloroplast or the mitochondria or the lumen of the endoplasmatic reticulum. During the translocation process, the targeting peptide is separated or proteolytically removed from the protein or subunit. A targeting sequence can be provided in the chimaeric gene to express a targeting peptide which can translocate an expressed protein of interest within a transformed plant cell as generally described in European patent applications ("EPA") 85402596.2 and 88402222.9. A suitable targeting peptide for transport into chloroplasts is the transit peptide of the small subunit of the enzyme 1,5-ribulose hisphosphate carboxylase (Krebbers et al (1988) Plant Mol. Biol. 11:745; EPA 85402596.2), but other chloroplast transit peptides, such as those listed by Watson (1984) Nucl. Acids Res. 12:5145 and Yon Heijne et al (1991) Plant Mol. Biol. Rep. 9:104, can also be used. Suitable mitochondrial targeting peptides are the mitochondrial transit peptides as described by Schatz (1987) Eur. J. Biochem. 165:1 and listed by Watson (1984) supra. Suitable targeting peptides that can translocate a protein of interest to the lumen of the endoplasmatic reticulum of a plant cell are, for instance, the signal peptides described by Von Heijne (1988) Biochem. Biophys. Acta 947:307 and listed by Watson (1984) supra.

Coding sequences that can be used for the production of transgenic dicotyledonous plants are well known (see, for example, the coding sequences listed in Weising et al (1988) Annual Rev. Genet. 22:421), and it is believed that such coding sequences can be put to equally good use in transformed monocotyledonous plants in accordance with this invention. In this respect, the coding sequences can be either foreign or endogenous to the plants and can, for example, code for proteins which: are toxic to insect species, thus protecting the plants against insect attack (EP 193259, EP 305275 and EP 358557); protect the plants against stress conditions (EP 359617); confer on the plants a resistance or tolerance to specific herbicides (EP 242236); kill or disable plant cells in which the proteins are expressed so that, when the coding sequences are under the control of a male or female organ-specific promoter, the proteins can render the plants respectively male sterile (EP 344029) or female sterile (EP 412006); can be extracted from the plants or selected plant organs and optionally be further processed so that the plants can be used as sources of economically important peptides or proteins (EP 319353); or are enriched in nutritionally important amino acids so that transformed plants or their organs, in which the proteins are expressed, can be used as food with enhanced nutritional value for animals or humans (EP 318341).

Coding sequences of particular usefulness for transforming monocots to render them insect-resistant are the genes isolated from *Bacillus thuringiensis* ("Bt") strains and truncated portions thereof that code for insecticidal crystal proteins and their insecticidal polypeptide toxins (for a review, see: Höfte and Whiteley (1989) Microbiol. Rev. 53:242). The following Bt genes are believed to be particularly important for insect control in cereals (e.g., corn, rice, wheat and barley): the CryIAb gene (EP 193259) and CryIAc gene for control of Helicoverpa species (e.g., *H. zea* and *H. armigera*); the CryIAb gene and the CryIb gene (EP 358557) for control of Ostrinia species (e.g., *O. nubilalis*) in corn; the CryIAc gene for the control of Agrotis species in corn and wheat; and the CryID and CryIE genes (EP 358557) for the control of Spodoptera species (e.g., *S. frugiperda*) in corn. To achieve sufficient expression of such genes in tissues of transgenic plants, it is preferred that the genes be modified as described in PCT application PCT/EP 91/00733 (PCT publication WO 91/16432).

Selectable markers in accordance with this invention are chimaeric genes in which the coding sequences encode proteins which confer on the plant cells, in which they are expressed, resistance to a selectable agent such as an antibiotic and/or herbicide. Screenable markers in accordance with this invention are chimaeric genes in which the coding sequences encode proteins which confer of the plant cells, in which they are expressed, a different appearance, such as a different color, making plants transformed with the screenable marker separable manually. The selection of a selectable or screenable marker, preferably a selectable marker, for transforming a monocotyledonous plant in accordance with this invention is not believed to be critical, and it is believed that conventional selectable and screenable markers can be used (see, for example, the markers listed in Weising et al (1988) supra). Examples of suitable coding sequences for selectable markers are: the neo gene (Beck et al (1982) Gene 19:327) that codes for the enzyme neomycin phosphotransferase which confers resistance to the antibiotic kanamycin; the hyg gene (Gritz and Davies (1983) Gene 25:179) that codes for the enzyme hygromycine phosphotransferase which confers resistance to the antibiotic hygromycin; and the bar gene (EP 242236) that codes for phosphinothricin acetyl transferase which confers resistance to the herbicide phosphinothricin. In using a selectable marker gene coding for a protein that confers tolerance or resistance to a herbicide or other selective agent that acts on chloroplast metabolism, such as the bar gene, it is preferred that the marker gene be part of a chimaeric gene together with a chloroplast targeting sequence as described above. Examples of suitable coding sequences for screenable markers are the gus gene (Jefferson et al (1986) Proc. Natl. Acad. Sci. USA 6:3901) encoding beta-glucuronidase and the luciferase gene (Ow et al (1986) Science 234:856).

As discussed above, the selection pressure, provided by the presence of a selectable agent, should preferably be rather high during culturing of transformed plant cells of this invention containing selectable markers. For example, when the neo gene is used as a selectable marker, kanamycin should be used in concentrations of at least about 100–200 mg per liter, preferably at least about 200 mg per liter, in the culture medium. Such high selection pressure should also be maintained for a prolonged time, for example, two to four months. It is believed, however, that particular selection pressures and durations are not critical and that the choice of selection pressures and their durations can be made in a conventional manner. However when the bar gene is used as a selectable marker gene, phosphinothricin (PPT) is preferably used in concentrations of 0.5 to 50, particularly 2 to 20, mg per liter of the culture medium.

Morphogenic sectors, preferably embryogenic sectors, of morphogenic callus, preferably compact embryogenic callus, produced in a culture of transformed cells of wounded and/or degraded intact tissue or wounded and/or degraded embryogenic sectors of compact embryogenic callus of this invention, can then be regenerated into phenotypically normal (e.g., mature and fertile) plants in a conventional manner (see, for example, references in Vasil (1988) supra and Lazzeri and Lörz (1988) supra). The regenerated plants, thus obtained, will be transgenic and will at least possess the selectable or screenable marker, preferably the selectable marker, stably integrated into their nuclear genome. The presence and expression of other genes of interest can then be evaluated in a conventional manner, such as by means of Southern blotting and/or by the polymerase chain reaction (Sambrook et al (1990) Molecular Cloning: A Laboratory Manual, Cold Spring Harbor Laboratory).

For the purposes of this invention, a phenotypically normal plant as produced by the transformation and regeneration procedures of this invention should be understood as at least one plant that does not differ substantially from an untransformed plant of the same line in any of its phenotypic characteristics except in those characteristics that are added or changed due to the expression of the DNA fragments introduced in the plant's genome during transformation. Of course, any procedure for transforming plants usually produces a number of transgenic plants that display a variety of phenotypes, only some of which are phenotypically normal as defined above.

The method of this invention can be applied to all monocotyledonous plant species from which compact morphogenic callus, such as compact embryogenic callus, can be obtained during in vitro culture of explants derived from various explant sources such as immature and mature zygotic embryos, leaf bases, young inflorescences, etc. The method will be especially useful for the transformation of economically important gramineous crops, particularly the major cereals, such as corn, wheat, rice, oats, barley, sorghum, rye and millet. The resulting transgenic plants of this invention can be used to create, in a rapid and efficient manner, novel lines and/or cultivars of high agronomic value. In this regard, transgenic plants can be created in accordance with this invention that can be used as pollinator plants, for example, as female-sterile pollinator plants for the production of hybrid seed as disclosed in EP 412006 (which is incorporated herein by reference).

This invention provides a rapid, efficient and reproducible method for transforming monocotyledonous plants, using intact tissue or compact embryogenic callus to produce cultures of transformed morphogenic callus, preferably compact embryogenic callus. This is surprising as neither intact tissue nor compact embryogenic callus has generally been regarded as a suitable starting material for obtaining stable transformants (see Vasil (1990) Bio/Technology 8:797). The use of intact tissue or compact embryogenic callus in accordance with this invention is a distinct improvement on existing monocot transformation methods 7 which have required the use of friable embryogenic callus, embryogenic cell suspension cultures and/or protoplasts that are competent for: 1) DNA uptake, 2) integrative transformation and 3) efficient and reproducible, monocotyledonous plant regeneration. Such requirements of competence have, up to now, limited stable transformations of monocots to plant lines with very specific tissue culture properties. In corn for example, only certain lines, such as the inbred line A188, have had the capacity to form enough type II callus (i.e., to form type II callus at frequencies higher than 10%, up to, for example, 80% or more), from which competent suspension cultures and/or protoplasts could be obtained at appreciable frequencies. However, all such corn lines have been of low agronomic value, so that transformations of economically valuable corn lines have only been possible by laborious breeding programs in which appropriate tissue culture properties have been transferred to the valuable corn lines from the transformable low value lines.

Because the method of this invention requires only a relatively short period of in vitro culture, the method is far less time and labor consuming than previous methods. The short tissue culture period also ensures that the occurrence of somaclonal variation is reduced.

The method of this invention provides novel, phenotypically normal (e.g., fertile), transgenic monocotyledonous plants, particularly gramineous plants, quite particularly cereals, most particularly corn and rice, which are transformed with at least one (e.g., foreign) gene of interest, stably integrated into their nuclear genome. The method is believed to be independent of the genotype of the plant, being transformed, and capable of transforming cells of any plant, from which compact embryogenic callus can be obtained from at least one of its tissues. This makes it possible to transform the majority of monocot species and a substantial number of lines within each species. Moreover, the capacity to form compact embryogenic tissue can be transferred, by means of classical breeding programs, from one line that posesses such capacity to another line that does not.

The novel transgenic monocot plants of this invention regenerated from transformed morphogenic callus, particularly transformed compact embryogenic callus, are characterized by the fact that from such monocots, using conventional culture conditions as described, for example, in Datta et al (1990) supra, Shimamoto et al (1989) supra, Hayashimoto et al (1990) supra, Gordon-Kamm et al (1990) supra, and Fromm et al (1990) supra, it is practically impossible to obtain embryogenic suspension cultures and/or protoplasts or it is practically impossible to obtain embryogenic suspension cultures and/or protoplasts which have sufficient capability of being stably transformed and then regenerated as phenotypically normal (e.g., fertile), transgenic plants. In regard to this second type of impossibility, it is not believed practical to obtain embryogenic suspension cultures or protoplasts of such monocots that: 1) have a high probability of being regenerable into phenotypically normal plants; 2) have a high probability of being competent with respect to DNA uptake and integrative transformation of the so taken-up DNA; and 3) when so transformed, have a high probability of being regenerable into phenotypically normal, transgenic plants.

In particular, this invention provides novel transgenic rice plants of rice lines, from which embryogenic suspension cultures (when obtainable) can generally be obtained, for example, according to the procedures described by Li et al (1990) Plant Mol. Biol. Report. 8:276, Datta et al (1990) Plant Sci. 67:83, and Datta et al (1990) Plant Cell Rep. 9:253, and protoplasts (when obtainable) can generally be obtained from the embryogenic suspension cultures, for example, according to the procedures described by Li and Murai (1990) Plant Cell Rep. 9:216. However under conventional culture conditions as described, for example, in Shimamoto et al (1989) supra, Datta et al (1990) supra and Hayashimoto et al (1990) supra, it is practically impossible to regenerate phenotypically normal (e.g., fertile) plants from embryogenic suspension cultures or protoplasts of such rice lines.

This invention also provides novel transgenic corn plants of corn lines, from which embryogenic suspension cultures (when obtainable) can generally be obtained, for example, according to the procedures described by Shillito et al (1989) Bio/Technology 7:581, Prioli and Söndahl (1989) Bio/Technology 7:589, Gordon-Kamm et al (1990) supra, and Fromm et al (1990) supra, and protoplasts (when obtainable) can generally be obtained from such embryogenic suspension cultures, for example, according to the procedures described by Shillito et al (1989) supra and Prioli and Söndahl (1989) supra. However under conventional culture conditions as described, for example, by Shillito et al (1989) supra, Prioli and Söndahl (1989) supra, Gordon-Kamm et al (1990) supra and Fromm et al (1990) supra, it is practically impossible to regenerate phenotypically normal (e.g., fertile) plants from embryogenic suspension cultures or protoplasts of such corn lines. Furthermore, such corn lines have the capacity to form type I callus at high frequencies but do not possess the ability to form type II callus at frequencies higher than 10%, particularly at frequencies higher than 1%, quite particularly at frequencies higher than 0.1%, more quite particularly at frequencies higher than 0.01. Type II corn callus is the only type of corn callus tissue, from which embryogenic suspension cultures and regenerable protoplasts can be suitably obtained that can be stably transformed, and thus, the inability to obtain type II callus for a particular corn line has meant, up to now, that one could not regenerate phenotypically normal (e.g., mature), transgenic corn plants from transformed callus of such corn line. The practical ability to obtain type II callus from a particular corn line can be assessed by the general procedures described by Gordon-Kamm et al (1990) supra and Fromm et al (1990) supra and the references mentioned therein. In making this assessment: callus cultures can be initiated from, for example, 1000 immature embryos of a corn line; the cultures can be maintained by subculturing every 3 weeks, and only those of the cultures that most resemble typical type II callus can be subcultured; and after 6 months, it can be determined at what frequencies a uniform type II callus is obtained.

More generally, to determine whether it is practical to obtain regenerable protoplasts from a specific line of a monocot species, the following well known procedures can be followed. In this regard, it is believed that regenerable protoplasts are most efficiently and reliably generated from embryogenic suspension cultures which, for any specific monocot, can be produced and maintained by conventional means. The extent and quality of an embryogenic suspension culture is generally dependent on its genotype, and it is generally only worthwhile to form protoplasts of a plant line, for transformation, if its embryogenic suspension culture is capable of plant regeneration. Embryogenic suspension cultures can generally be characterized as consisting of well dispersed, small groups of richly cytoplasmic embryogenic cells, as being free of callus tissues or organized meristems, as having cell doubling times of 27–32 hours, and as being capable of forming somatic embryos and plants (Vasil (1988) Bio/Technology 6:397). It can be determined whether an embryogenic suspension culture of a particular line of a monocot species is suitable for plant regeneration by plating a large number (i.e., at least 100) of cell aggregates on a suitable regeneration medium and determining what proportion of the aggregates give rise to phenotypically normal, fertile plants. If normal fertile plants are obtained from 50% or more of the cell aggregates, it is generally considered worthwhile to proceed with protoplast generation. However, a specific monocot line can be considered as not being suitable for providing regenerable protoplasts suitable for plant transformation if, using conventional protoplast isolation, culture, and plant regeneration techniques: for every 10,000 protoplasts, no more than about 500, especially no more than about 100, particularly no more than about 10, quite particularly no more than about 1, phenotypically normal (e.g., fertile) plant(s) can be regenerated.

The Examples, which follow, illustrate this invention. Unless otherwise indicated, all experimental procedures for manipulating recombinant DNA were carried out by the standardized procedures described in Sambrook et al (1990) Molecular Cloning: A Laboratory Manual, Cold Spring Harbor Laboratory. Oligonucleotides were designed according to the general rules outlined by Kramer and Fritz (1968) Methods in Enzymology 154:350 and synthesized by the phosphoramidite method of Beaucage and Caruthers (1981) Tetrahedron Letters 22:1859 on an Applied Biosystems 380A DNA synthesizer (Applied Biosystems B.V., Maarssen, Netherlands). The following bacterial strains and plasmids, used in the Examples, are available from the Deutsche Sammlung for Mikroorganismen und Zellkulturen ("DSM"), Mascheroder Weg 1B, Braunschweig, Germany:

| Bacterial strain | plasmid | DSM No | Date of Deposit |
|---|---|---|---|
| E. coli WK6 | pMa5-8 | DSM 4567 | May 3, 1988 |
| E. coli WK6 | pMc5-8 | DSM 4566 | May 3, 1988 |

EXAMPLE 1

Transformation of corn with a selectable marker gene by electroporation of DNA into zygotic immature embryos Zygotic immature embryos of about 0.5 to 1 mm were isolated from developing seeds of two corn inbred lines, Pa91 and H99. The freshly isolated embryos were enzymatically treated for 1–2 minutes with an enzyme solution II (0.3% macerozyme (Kinki Yakult, Nishinomiya, Japan) in CPW salts (Powell & Chapman (1985) "Plant Cell Culture, A Practical Approach", R. A. Dixon ed., Chapter 3) with 10% mannitol and 5 mM 2-[N-Morpholino] ethane sulfonic acid (MES), pH 5.6). After 1–2 minutes incubation in this enzyme solution, the embryos were carefully washed with N6aph solution (macro- and micro-elements of N6 medium (Chu et al (1975) Sci. Sin. Peking 18:659) supplemented with 6 mM asparagine, 12 mM proline, 1 mg/l thiamine-HCl, 0.5 mg/l nicotinic acid, 100 mg/l casein hydrolysate, 100 mg/l inositol, 30 g/l sucrose and 54 g/l mannitol). After washing, the embryos were incubated in the maize electroporation buffer, EPM-NaCl (150 mM NaCl, 5 mM $CaCl_2$, 10 mM HEPES (N-2-hydroxyethylpiperazine-N'-2-ethanesulfonic acid) and 0,425M mannitol, pH 7.2). Approximately 100 embryos in 200 µl EPM-NaCl were loaded in each cuvette. About 20 µg of a plasmid DNA, pDE108 linearized with HindIII, were added per cuvette. pDE108 is a 5399 bp plasmid, the entire sequence of which is set forth in Seq. Id. No. 1 and which contains a chimaeric gene comprising the kanamycin resistance gene (neo) under the control of the 35S3 promoter (EP 359617).

After 1 hour DNA incubation with the explants, the cuvettes were transferred to an ice bath. After 10 minutes incubation on ice, the electroporation was carried out: one pulse with a field strength of 375 V/cm was discharged from a 900 µF capacitor. The electroporation apparatus was as described by Dekeyser et al (1990) The Plant Cell 2:591. Immediately after electroporation, fresh liquid N6aph substrate was added to the explants in the cuvette, after which the explants were incubated for a further 10 minute period on ice.

Afterwards, the embryos were transferred to Mah1 VII substrate (macro- and micro-elements and vitamins of N6 medium supplemented with 100 mg/l casein hydrolysate, 6 mM proline, 0.5 g/l MES, 1 mg/l 2,4-dichlorophenoxyacetic acid (2,4-D) and 2% sucrose solidified with 0.75 g/l $MgCl_2$ and 1.6 g/l Phytagel (Sigma Chemical Company, St Louis, Mo. U.S.A.), pH 5.8) and supplemented with 0.2M mannitol. After 3 days for line H99 and 2 days for line Pa91, the embryos were transferred to the same substrate supplemented with 200 mg/l kanamycin. After approximately 14 days, the embryos were transferred to Mah1 VII substrate without mannitol, supplemented with kanamycin. The embryos were further subcultured on this selective substrate for approximately 2 months with subculturing intervals of about 3 weeks. The induced embryogenic tissue was carefully isolated and transferred to MS medium (Murashige and Skoog (1962) Physiol. Plant 15:473) supplemented with 5 mg/l 6-benzylaminopurine for line H99 and 5 mg/l zeatin for line Pa91. The embryogenic tissue was maintained on this medium for approximately 14 days and subsequently transferred to MS medium without hormones and 6% sucrose for line H99 and 3% sucrose for line Pa91. Developing shoots were transferred to ½ MS medium with 1.5% sucrose for further development to normal plantlets. These plantlets were transferred to soil and cultivated in the greenhouse.

EXAMPLE 2

Characterization of the transformed corn plants of Example 1

Seventeen plants from Example 1 were analysed for the presence of the chimaeric neo gene by means of the polymerase chain reaction (PCR). DNA was prepared according to the protocol described by Dellaporta et al (1983) Plant Mol. Biol. Reporter 1:19, adapted for application to tissue amounts of about 10 to 20 mg. For each plant, such an amount of tissue was macerated in extraction buffer in a microfuge tube. A 706 bp fragment, corresponding to part of the coding sequence of the neo gene, was amplified with the polymerase chain reaction according to the protocol described by Sambrook et al (1990) supra, using oligonucleotide probes complementary to the sequences of plasmid pDE108 from nucleotide 1384 to 1406 and 2089 to 2067 (numbering as in Seq. Id. No. 1). In total, 35 cycles with an annealing temperature of 50° C. were carried out. The final DNA was analysed by electrophoresis on a 1.5% agarose gel. A 706 bp fragment could be identified in a total of 13 plants. One of the positive plants died at a later stage.

Figure 1:
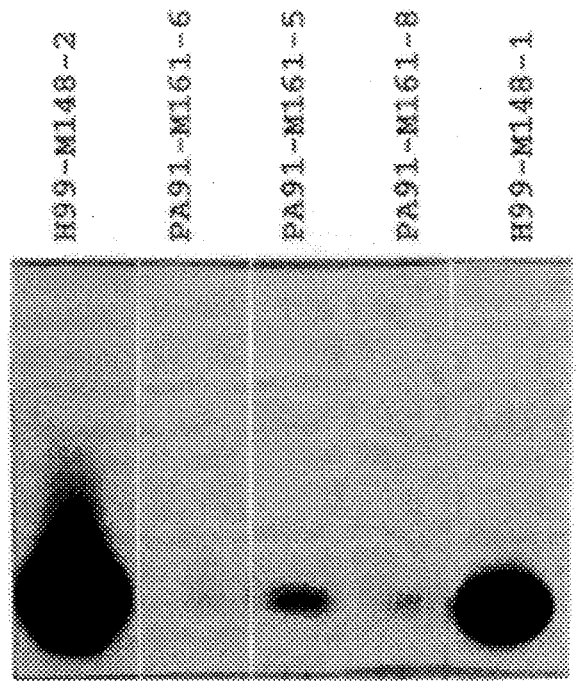
FIG. 1: NPTII gel assays of Example 2 of five corn transformants obtained by electroporation of immature zygotic embryos.

Activity of the expression product of the neo gene (i.e., neomycin phosphotransferase II (NPTII)) was assayed in 9 of the plants as follows. Crude extracts were prepared by grinding plant tissue in extraction buffer (McDonnell et al (1987) Plant Molecular Biol. Reporter 5:380). The extracts were then subjected to non-denaturing polyacrylamide gel electrophoresis according to the procedure described by Reiss et al (1984) Gene 30:211. NPTII activity was then assayed by in situ phosphorylation of kanamycin using [gamma-$^{32}$P]ATP as a substrate (McDonnell et al (1987) supra). NPTII activity was found in 8 of the plants that were examined (FIG. 1).

Figure 2:
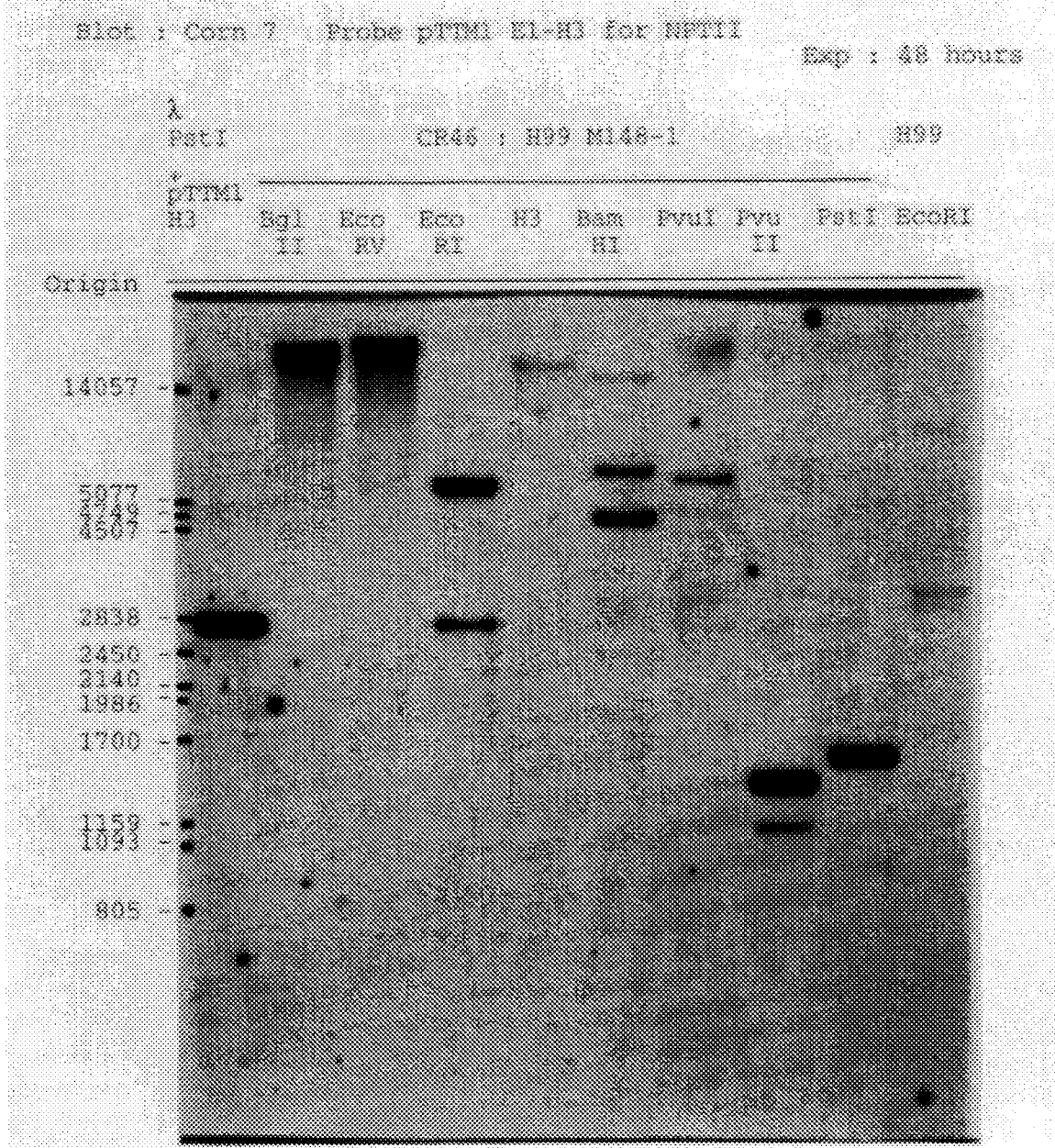
FIG. 2: Southern blots of Example 2 of genomic DNA of one of the corn transformants of Example 1 (H99-M148-1), using the sequence listed as Seq. Id. 2 as a probe. Lengths of standard fragments are indicated. The origin is indicated by 0.

One of the plants (H99-M148-1), that was found to be positive on both the PCR and NPTII assay, was further analyzed by means of Southern hybridization. Genomic DNA was prepared from plant tissue according to the protocol described by Dellaporta et al (1983) supra supplemented by a treatment with RNase to remove remaining RNA. A non-transformed H99 plant was used as a control. Samples of the DNA were digested with one of the following restriction enzymes: BglII, EcoRI, EcoRV, HindIII, BamHI, PvuI, PvuII or PstI and subjected to horizontal agarose electrophoresis. Southern transfer to Hybond N+ (Amersham International PLC, Amersham, United Kingdom) membranes by means of the "alkali blotting of DNA" protocol and the subsequent hybridization were performed as recommended by the manufacturer (Amersham Hybond-N+ leaflet). Radioactive probes were prepared with the multi-prime DNA labelling kit (Amersham) according to the protocol supplied by the manufacturer which was derived from published procedures (Feinberg and Vogelstein (1983) Anal. Biochem. 132:6). As a probe, a 1184 bp EcoRI-HindIII fragment derived from another plasmid was used. The sequence of this plasmid is given in Seq. Id. No. 2. The banding patterns (e.g., see FIG. 2) showed that at least the chimaeric neo gene was integrated into the plant genomic DNA.

Further analysis of this transformed plant (H99-m148-1) showed that it carries two almost intact copies of the plasmid pDE108 and part of a third rearranged copy. The two almost complete copies are apparently inserted in the plant genome in a head to tail concatamer configuration. However, some rearrangements must have occurred as an additional NcoI site and an additional BglII site were created, while the HindIII site (used for linearization of pDE108 prior to electroporation) at the junction of the two copies was lost. Sequencing of the junction of the two plasmid copies, as integrated in the plant genome, revealed that only the protruding 5' termini of the HindIII site are missing, thus creating a NcoI site as follows [SEQ ID NO:5]:

(the lost bases are underlined, and the created NcoI site at the junction is highlighted). Additional analysis showed that no or very few plasmid DNA sequences around the HindIII sites, flanking the plant genome, were lost. Although the other plants were not tested in this way, the PCR and NPTII assays showed that the chimaeric genes are present and expressed.

The mature transformed plants were fertile and phenotypically completely normal. The plant that was previously assayed by Southern hybridization was used as pollinator plant in three crossings with untransformed plants (two from corn inbred line H99 and one from corn inbred line Pa91). A total of 44 of the plants of the F1 progeny were assayed for NPTII activity as described above, and twenty of them were found to be positive. This does not differ significantly from the 1:1 ratio expected under normal Mendelian segregation assuming that the transformed pollinator plant had one active copy (or alternatively, multiple closely linked active copies) of the chimaeric neo gene ($X^2=0.36$).

EXAMPLE 3

Transformation of corn with a selectable marker gene by electroporation of DNA into type I callus derived from immature zygotic embryos Immature zygotic embryos of about 0.5 to 1 mm in length were isolated from developing seeds of the corn inbred line Pa91 and cultured on Mah1 VII substrate with subsequent subculture intervals of about 14 days. Embryogenic tissue was carefully dissected out from developing type I callus. The embryogenic tissue in EPM (EPM-NaCl without NaCl) was then finely cut in fragments with a maximum length of about 1.5 mm. The resulting callus fragments were preplasmolysed for three hours in this buffer. After three hours, the callus fragments were transferred to EPM-NaCl. About 100–150 mg of callus fragments were transferred to 200 µl EPM-NaCl per cuvette. 20 µg DNA of plasmid pDE108 (Seq. Id. No. 1), linearized with HindIII, was added to each cuvette. The DNA was incubated with the callus fragments for one hour, after which the cuvettes were transferred to an ice bath.

After 10 minutes incubation on ice, the electroporation was carried out: one pulse with a field strength of 375 V/cm was discharged from a 900 µF capacitor. The electroporation apparatus was as described by Dekeyser et al (1990) supra. Immediately after electroporation, fresh liquid N6aph substrate, supplemented with 6mM asparagine, 12 mM proline, 1 mg/l thiamine-HCl, 0.5 mg/l nicotinic acid, 100 mg/l casein hydrolysate, 100 mg/l inositol, 30 g/l sucrose and 54 g/l mannitol, was added to the callus fragments which were then further incubated for 10 minutes on ice.

After one day culture in liquid N6aph substrate supplemented with 1 mg/l 2,4-D, the callus fragments were transferred to Mah1 VII substrate supplemented with 0.2M mannitol and 200 mg/l kanamycin. Fourteen days later, the callus fragments were subcultured on the same selective substrate but without mannitol and further cultured on this substrate for about 2 months with subculturing intervals of about 3 weeks. The embryogenic sectors of the resulting calli were isolated from the slimy tissue and transferred to MS substrate (Murashige and Skoog (1962) Physiol. Plant 15:473) with 3% sucrose and supplemented with 5 mg/l zeatin to germinate. Tissue was maintained on this medium for approximately 2 weeks and subsequently transferred to MS medium with 3% or 6% sucrose. Shoots that developed on this substrate were transferred to half-strength MS medium with 1.5% sucrose for further development to normal plantlets. These plantlets were transferred to soil and cultivated in the greenhouse.

EXAMPLE 4

Characterization of the transformed corn plants of Example 3

Twenty nine plants from Example 3 were analysed for the presence of the chimaeric neo gene by means of the polymerase chain reaction. DNA was prepared according to Dellaporta et al (1983) Plant Mol. Biol. Reporter 1:19, adapted for application to tissue amounts of about 10 to 20 mg. For each plant, such an amount of tissue was macerated in extraction buffer in a microfuge tube. A 706 bp fragment, corresponding to part of the coding sequence of the neo gene, was amplified with the polymerase chain reaction according to the protocol described by Sambrook et al (1990) supra, using oligonucleotide probes complementary to the sequences of plasmid pDE108 from nucleotide 1384 to 1406 and 2089 to 2067 (numbering as in Seq. Id. 1). In total, 35 cycles with an annealing temperature of 50° C. were carried out. The final DNA was analysed by electrophoresis on a 1.5% agarose gel. A 706 bp fragment could be identified in a total of 14 plants. One of the positive plants died at a later stage.

Activity of the NPTII expression product of the neo gene was assayed in 24 of the plants as follows. Crude extracts were prepared by grinding plant tissue in extraction buffer (McDonnell et al (1987) Plant Molecular Biol. Reporter 5:380). The extracts were then subjected to non-denaturing polyacrylamide gel electrophoresis according to the procedure described by Reiss et al (1984) Gene 30:211. NPTII activity was then assayed by in situ phosphorylation of kanamycin using [gamma-32P]ATP as a substrate (McDonnell et al, supra). NPTII activity was found in 14 of the plants that were examined (FIG. 3). Two plants that were NPTII positive scored negative in a PCR assay.

Two of the plants (Pa91-M146-2 and Pa91-M149-1), that were found to be positive on both the PCR and NPTII assays, were further analyzed by means of Southern hybridization. Genomic DNA was prepared from plant tissue according to Dellaporta et al (1983) supra, supplemented by a treatment with RNase to remove remaining RNA. A non-transformed Pa91 plant was used as control. Samples of the DNA were digested with one of the following restriction enzymes: BglII, EcoRI, EcoRV, HindIII, BamHI, PvuI, PvuII or PstI and subjected to horizontal agarose electrophoresis. Southern transfer to Hybond N+ membranes by means of the "alkali blotting of DNA" protocol and the subsequent hybridization were performed as recommended by the manufacturer (Amersham). Radioactive probes were prepared with the multi-prime DNA labelling kit (Amersham) according to the protocol supplied by the manufacturer which was derived from published procedures (Feinberg and Vogelstein (1983) Anal. Biochem. 132:6). As a probe, a 1184 bp EcoRI-HindIII fragment derived from another plasmid was used. The sequence of this plasmid is given in Seq. Id. No. 2. The banding patterns (e.g., see FIG. 4) showed that at least the chimaeric neo gene was integrated into the plant genomic DNA.

Further analysis of one of the transformed plants (Pa91-M146-2) showed that it carried two almost intact copies of the plasmid pDE108 in a head to tail configuration. The HindIII site (used for linearization of pDE108 prior to electroporation) at the junction of the two copies was lost. Sequencing of the junction of the two plasmid copies, as integrated in the plant genome, revealed that the protruding 5' termini of the HindIII site plus one base downstream of one of the HindIII sites are missing as follows:

| AGCCA | + | AGCTTGGCG | = | AGCCATGGCG |
| TCGGTTCGA | | ACCGC | | TCGGTACCGC |

(the lost bases are underlined). Additional analysis showed that no or very few plasmid DNA sequences around the HindIII sites, flanking the plant genome, were lost. Although the other plants were not tested in this way, the PCR and NPTII assays showed that the chimearic genes are present and expressed.

The adult plants were fertile and phenotypically completely normal. One of the plants, previously assayed by Southern hybridization, was used as a pollinator plant in a crossing with an untransformed plant from the corn inbred line H99. A total of 20 plants of the F1 progeny were assayed for NPTII activity as described above, and six of them were found to be positive. This does not differ significantly from the 1:1 ratio expected under normal Mendelian segregation assuming that the transformed pollinator plant had one active copy of the chimaeric neo gene ($X^2=3.2$).

EXAMPLE 5

Transformation of corn with a male-sterility gene and a selectable marker by gene electroporation of DNA into zygotic immature embryos Zygotic immature embryos of about 1 to 1.5 mm were isolated from developing seeds of corn inbred line H99. Freshly isolated embryos were enzymatically treated and washed as described in Example 1. After washing, the embryos were loaded in the maize electroporation buffer, EPM-KCl (80 mM KCl, 5 mM $CaCl_2$, 10 mM HEPES and 0.425M mannitol, pH 7.2). Approximately 100 embryos in 200 µl EPM-KCl were loaded in each cuvette. About 20 µg of a plasmid DNA, pVE107 linearized with HindIII, were added per cuvette. pVE107 is a 6659 bp plasmid which is obtained by ligation of the 1287 bp EcoRV-EcoRI fragment of pTTM8 (EP 344029; Seq. Id. No. 3) to the large XbaI (filled-in with Klenow)-EcoRI fragment of plasmid pDE108 (Seq. Id. No. 1). pVE107 contains: a chimaeric gene comprising the kanamycin resistance gene (neo) under the control of the 35S3 promoter; and another chimaeric gene comprising the barnase gene (Hartley (1988) J. Mol. Biol. 202:913) under the control of the tapetum-specific promoter of the TA29 gene of Nicotiana tabacum (EP 344029).

All vector constructions involving fragments of the barnase gene were carried out in E. coli strain WK6 containing the plasmid pMc5BS. pMc5BS contains the barstar gene (encoding an inhibitor of barnase) under the control of the tac promoter (De Boer et al (1983) Proc. Natl. Acad. Sci. USA 80:21). This plasmid is constructed by: cloning the EcoRI-HindIII fragment of plasmid pMT416 (see Hartley (1988) supra) into the EcoRI and HindIII sites of plasmid pMc5-8 (DSM 4566); and then deleting the sequence, starting with the initiation codon of the phoA signal sequence and ending with the last nucleotide before the translation initiation codon of the barstar coding region, by means of a looping-out mutagenesis procedure as generally described by Sollazo et al (1985) Gene 37:199.

After a 1 hour DNA incubation with the explants, the cuvettes were transferred to an ice bath. After 10 minutes incubation on ice, the electroporation was carried out as described in Example 1. Immediately after electroporation, fresh liquid N6aph substrate was added to the explants in the cuvette, after which the explants were incubated for a further 10 minute period on ice.

Afterwards, the embryos were transferred to Mah1 VII substrate supplemented with 0.2M mannitol and 200 mg/l kanamycin. After approximately 14 days, the embryos were transferred to Mah1 VII substrate without mannitol but with the same selective agent, kanamycin. The embryos were further subcultured on this selective substrate for approximately 2 months, with subculturing intervals of about 3 to 4 weeks. The induced embryogenic tissue was carefully isolated and transferred to MS medium (Murashige and Skoog (1962) supra) supplemented with 5 mg/l 6-benzylaminopurine. The embryogenic tissue was maintained on this medium for approximately 14 days and subsequently transferred to MS medium without hormones and sucrose. Developing shoots were transferred to ½ MS medium with 1.5% sucrose for further development to normal plantlets. These plantlets were transferred to soil and cultivated in the greenhouse.

EXAMPLE 6

Characterization of the transformed corn plants of Example 5

Seven plants from Example 5, designated RZM19-2, RZM19-3, RZM19-4, RZM19-5, RZM19-6, RZM19-7 and RZM19-8, were derived from the same embryogenic callus clump. They were subjected to extensive Southern analysis. In this regard, BamHI-NcoI digested genomic DNA of the plants was probed with pVE107 and with the small EcoRV-XbaI fragment of pTTM8 (containing PTA29-barnase; see Seq. Id. No. 3). In all plants, the strongest detected band was the expected 1400 bp fragment. However, the pattern found in these and other southern blots was very complex and indicated that transformation had resulted in many insertions of all or part of pVE107 into the plants' genomes. Some of the inserted copies of pVE107 were apparently incomplete and/or had undergone rearrangements. However, the same complex integration pattern was found in all seven plants. This could be explained by the fact that the seven transformants were all derived from one embryogenic callus clump.

The transformed plants were male sterile but otherwise phenotypically completely normal; female fertility, for instance, was normal. The spikelets of the male flowers were of about normal length but were very thin and appeared to be empty, and they never opened. A detailed analysis showed that the anthers were reduced to almost microscopic structures. This phenotype indicates not only that at least one copy of the barnase gene was expressed but also that it was selectively expressed in some or all of the tissues of the anthers.

Transformant RZM19-3 was pollinated with pollen from an untransformed H99 plant, and 53 progeny plantlets were recovered. Of these 53 plantlets, 32 (60%) scored positive in a NPTII assay, while 21 (40%) were NPTII negative. This proportion in the F1 progeny does not differ significantly from the 1:1 ratio expected under normal Mendelian segregation assuming that the transformed female parent had one active copy of the chimaeric neo gene ($X^2=2.28$). The NPTII negative progeny were male fertile, while the NPTII positive progeny were male sterile.

31 NPTII positive progeny plants were subjected to Southern analysis. 28 of these plants displayed the same integration pattern as that of the original transformant, RZM19-3, from which they were derived. 3 plants had a slightly altered pattern.

EXAMPLE 7

Transformation of corn with a male-sterility gene and a herbicide resistance gene by electroporation of DNA into zygotic immature embryos Zygotic embryos of corn inbred line H99 were isolated, enzymatically treated, washed, and loaded in electroporation buffer as described in Example 5. Approximately 100 embryos in 200 µl EPM-KCl were loaded in each cuvette. About 20 µg of a plasmid DNA, pVE108 linearized with HindIII, was added per cuvette. pVE108 is a 5620 bp plasmid which is obtained by ligation of the 1287 bp EcoRV-EcoRI fragment of pTTM8 (EP 344029; Seq. Id. No. 3) to the large EcoRI-StuI fragment of plasmid pDE110 (Seq Id. No. 4). pVE108 contains: a chimaeric gene comprising the bar gene (EP 242236), encoding phosphinothricin acetyl transferase (PAT) and conferring resistance to an herbicidal glutamine synthetase inhibitor such as phosphinothricin (PPT), under the control of the 35S3 promoter; and another chimaeric gene comprising the barnase gene (Hartley (1988) supra) under the control of the tapetum-specific promoter of the TA29 gene (EP 344029) of *N. tabacum*. All vector constructions involving DNA fragments comprising the barnase gene were carried out in *E. coli* strain WK6 containing the plasmid pMc5BS of Example 5.

After a 1 hour DNA incubation with the explants, the cuvettes were transferred to an ice bath. After 10 minutes incubation on ice, the electroporation was carried out as described in Example 1. Immediately after electroporation, fresh liquid N6aph substrate was added to the explants in the cuvette, after which the explants were incubated for a further 10 minute period on ice.

Afterwards, the embryos from one electroporation experiment were transferred to Mah1 VII substrate supplemented with 0.2M mannitol and 2 mg/l PPT. After approximately 14 days, the embryos were transferred to Mh1 VII substrate (Mah1 VII substrate of Example 1 but without proline and casein hydrolysate) supplemented with 2 mg/l PPT but without mannitol. After approximately 4 weeks, the embryos were subcultured for another month on Mh1 VII substrate supplemented with 10 mg/l PPT. The induced embryogenic tissue was carefully isolated and transferred to MS medium supplemented with 5 mg/l 6-benzylaminopurine. The embryogenic tissue was maintained on this medium for approximately 14 days and subsequently transferred to MS medium without hormones and sucrose. Developing shoots were transferred to ½ MS medium with 1.5% sucrose for further development to normal plantlets. These plantlets survived an in vitro spraying with doses of BASTA® (Hoechst AG, Frankfurt am Main, Germany) corresponding to 2 l/ha. These plantlets were then transferred to soil and cultivated in the greenhouse, and two of the transformed plantlets, designated RZM35-1 and RZM35-18, were further characterized (see Example 8).

The embryos from a second eletroporation experiment were transferred to Mh1 VII substrate supplemented with 2 mg/l PPT and 0.2M mannitol. After about 14 days, the embryos were transferred to Mh1 VII substrate supplemented with 2 mg/l PPT but without mannitol. After approximately another three weeks, the embryos were transferred to Mh1 VII substrate supplemented with 10 mg/l PPT but without mannitol. After another three weeks, the induced embryogenic tissue was carefully isolated and transferred to MS medium supplemented with 2 mg/l PPT and 5 mg/l 6-benzylaminopurine. The embryogenic tissue was maintained on this medium for approximately 14 days and subsequently transferred to MS medium without hormones, sucrose or PPT. Developing shoots were transferred to ½ MS medium with 1.5% sucrose for further development to normal plantlets. The resulting plantlets were transferred to soil and cultivated in the greenhouse, and three of the transformed plantlets, designated RZM34-1, RZM34-12, and RZM34-14, were further characterized (see Example 8).

EXAMPLE 8

Characterization of the transformed corn plants of Example 7

RZM34-1, RZM34-12, RZM34-14, RZM35-1, and RZM35-18 of Example 7 were grown in the greenhouse. Activity of the expression product of the bar gone in leaves of the plants was assayed as follows in a "PAT assay". 100 mg of leaf tissue from each plant, together with 50 mg of acid-treated sea sand (Merck, Darmstadt, Germany) and 5 mg polyvinylpolypyrrolidone (PVPP), were ground in an Eppendorf tube with a glass rod in 50 µl of extraction buffer (25 mM Tris-HCL pH 7.5, 1 mM $Na_2$-EDTA (ethylenediaminetetraacetic acid disodium salt), 0.15 mg/ml phenylmethylsulfonylfluoride (PMSF), 0.3 mg/ml dithiothreitol (DTT), and 0.3 mg/ml bovine serum albumin). The extract was centrifuged in a microfuge for 5 minutes at 16000 rpm. The supernatant was recovered and diluted ten times with TE 25/1 (25 mM Tris-HCL pH 7.5, 1 mM $Na_2$-EDTA. To twelve µl of the diluted extract was then added: 1 µl of 1 mM PPT in TE 25/1, 1 µl of 2 mM ActeylCoenzyme A in TE 25/1, and 2 µl of [$^{14}$C] AcetylCoenzym A (60 mCi/mmol, 0.02 mCi/ml, [NEN Research Products, DUPONT, Wilmington, Del., USA). The reaction mixture was incubated for 30 minutes at 37° C. and spotted on a aluminium sheet silicagel 60 t.l.c. plate with concentrating zone (Merck). Ascending chromatography was carried out in a 3 to 2 mixture of 1-propanol and $NH_4OH$ (25% $NH_3$). $^{14}$C was visualized by overnight autoradiography (XAR-5 Kodak film).

The tolerance to the herbicide BASTA® was tested by brushing a small area near the top of one leaf per plant with a 1% solution of the herbicide and observing the damage symptoms at and near the brushed sites. While RZM34-1, RZM35-1 and RZM35-18 showed no damage symptoms at all, RZM34-12 and RZM34-14 displayed slight browning and drying-out of the brushed site.

RZM34-1, RZM34-12, RZM34-14, RZM35-1 and RZM35-18 were also shown to be male sterile. The phenotype of each of these plants was identical to that described for the transformants of Example 5 which were analyzed in Example 6.

Southern analysis showed RZM35-1 and RZM35-18 to have an identical integration pattern, with only one copy of plasmid pVE108 being present in the genome of each. A small pan of the plasmid DNA sequence adjacent to the HindIII site (used for linearization prior to electroporation) seemed to be absent in the integrated copy. Southern analysis of RZM34-1, RZM34-12 and RZM34-14 showed that each of these plants probably has two or three copies of part or all of pVE108 integrated into its genome. The copies are most likely not inserted in a concatemer configuration.

Transformants RZM35-1 and RZM34-1 were pollinated with pollen from an untransformed H99 plant and progeny plantlets were recovered. From the 35 plantlets recovered from RZM35-1, 16 (46%) scored positive in a PAT assay, while 19 (54%) were PAT negative. This proportion in the F1 progeny does not differ significantly from the 1:1 ratio expected under normal Mendelian segregation of one active copy of the chimaeric bar gene ($X^2=0.26$).

From the 34 plantlets recovered from RZM34-1, 19 (56%) scored positive in a PAT assay, while 15 (44%) were PAT negative. This proportion in the F1 progeny does not differ significantly from the 1:1 ration expected under normal Mendelian segregation assuming that the transformed female parent had one active copy, or alternatively multiple active, but closely linked copies, of the chimaeric bar gene ($X^2=0.47$).

EXAMPLE 9

Transformation of rice with a herbicide resistance gene by electroporation of DNA into compact embryogenic callus derived from dry seeds Dehusked mature seeds of the rice cultivar Nipponbare were surfaced-sterilized, placed on solid 2N6 medium (N6 medium (Chu et al (1975) supra), supplemented with 0.5 mg/l nicotinic acid, 0.5 mg/l pyridoxine-HCl, 1.0 mg/l thiamine-HCl, 2.0 mg/l 2, 4-D, 30 g/l sucrose, and 2.0 g/l Phytagel, pH 5.8), and cultured at 27° C. in the dark. Callus developed from the scutella of the embryos within 3–4 weeks. Embryogenic portions of primary callus were transferred to N67 medium (N6 medium (Chu et al (1975) supra), supplemented with 0.5 mg/l nicotinic acid, 0.5 mg/l pyridoxine-HCl, 1.0 mg/l thiamine-HCl, 2.0 g/l casamino acids (vitamin assay, Difco), 1.0 mg/l 2,4-D, 0.5 mg/l 6-benzylaminopurine, 20 g/l sucrose, 30g/l sorbitol, and 2.0 g/l Phytagel, pH 5.8) for propagation into compact embryogenic callus.

Three to four weeks after subculture, the embryogenic callus was used for transformation experiments. The callus was cut into fragments with a maximum length of about 1.5 to 2 mm. The callus pieces were washed twice in EPM and then preplasmolyzed in this buffer for 30 minutes to 3 hours at room temperature (25° C.). Then, the callus fragments were washed twice with EPM-KCl and transferred to electroporation cuvettes. Each cuvette was loaded with about 150 to 200 mg of callus fragments in 100 to 200 μl EPM-KCl. 10 to 20 μg of a plasmid DNA, either circular pDE110 or pDE110 linearized with HindIII or EcoRI, were added per cuvette. pDE110 is a 4883 bp plasmid, the entire sequence of which is set forth in Seq. Id. No. 4 and which contains a chimaeric gene comprising the bar gene under the control of the 35S3 promoter.

The DNA was incubated with the callus fragments for about 1 hour at room temperature. Electroporation was then carried out as described in Example 1. After electroporation, liquid N67 medium without casamino acids was added to the callus fragments. The callus fragments were then plated on solid N67 medium without casamino acids but supplemented with 5, 10 or 20 mg/l PPT and were cultured on this selective medium at 27° C. under a light/dark regime of 16/8 hours for about 4 weeks. Developing PPT-resistant calli were isolated and subcultured for about two to three weeks onto fresh N67 medium without casamino acids but containing 5 mg/l PPT. Thereafter, selected PPT-resistant calli were transferred to plant regeneration medium N6M25 (N6 medium (Chu et al (1975) supra), supplemented with 0.5 mg/l nicotinic acid, 0.5 mg/l pyridoxine-HCl, 1.0 mg/l thiamine-HCl, 288 mg/l aspartic acid, 174 mg/l arginine, 7.0 mg/l glycine, 1.0 mg/l O-naphthalenacetic acid (NAA), 5.0 mg/l kinetin, 20 g/l sucrose and 2.0 g/l Phytagel, pH 5.8) supplemented with 5 mg/l PPT. Plantlets developed within approximately 1 month and were then transferred to hormone-free N6 medium (Chu et al (1975) supra), supplemented with 0.5 mg/l nicotinic acid, 0.5 mg/l pyridoxin-HCl, 1.0 mg/l thiamine-HCl, 1.0 g/l casamino acids, 20 g/l sucrose, and 2.0 g/l Phytagel, pH 5.8) on which they were kept for another 2 to 3 weeks, after which they were transferred to soil and cultivated in the greenhouse.

The compositions of the 2N6, N67, N6M25 and hormone-free N6 media, described above, were kindly provided by Japan Tobacco Inc., Plant Breeding and Genetics Research Laboratory, 700 Higashibara, Toyoda, Iwata, Shizuoka 438, Japan.

EXAMPLE 10

Characterization of the transformed rice plants of Example 9

Two transformed rice plants of Example 9, obtained in different transformation experiments, were cultivated for four weeks in soil and were then sprayed with BASTA® at a dosage corresponding to 2 1/ha. The two plants were BASTA® resistant and survived the herbicide treatment whereas non-transformed control plants turned brown and died within four days of herbicide spraying.

The two plants and four other in vitro plantlets, derived from two further transformation experiments of Example 9, were analyzed by means of a Southern hybridization in which plnat genomic DNA, digested with PvuII, was probed with pDE110. This analysis showed that, in all analyzed plants, at least part of one copy of pDE110 was integrated in the rice genome. In five out of six plants, the 1.6 kb fragment coresponding to the pDE110 fragment containing most of the 35S-bar chimaeric gene could be unambiguously identified.

EXAMPLE 11

Field tests with the transformed corn plants of Examples 2 and 4

The progeny of the corn transformant H99-M148-1 of Example 2 and of the corn transformant Pa91-M146-2 of Example 4 were tested under field conditions at the Plant Genetic Systems, N.V. experimental farm in Afsnee, Belgium. The field trial was authorized by the Belgian Ministry of Agriculture under registration number BIOT/91/M06. F1, F2, and F3 progeny were obtained from crosses as summarized in Table 1, below. In all cases one of the parents was assumed to be a heterozygote for the neo gene.

Up to 100 seeds of each seedlot were planted in 5 parellel rows, each with a length of 5 meters. Individual plants were 0.25 m apart, and the distance between rows was 1 m. 10 rows of experimental plants were alternated with 1 row of non-transformed H99 and 1 row of non-transformed Pa91 plants as controls. One plot consisted of F1 and F2 experimental plants with controls. Each of these plots was surrounded by i) a path with a width of 1 m and ii) 3 rows (1 m apart) of non-transformed corn plants (variety Sanora).

Experimental plots were prepared, sowed and maintained according to the schedule in Table 2, below. For sowing, plant holes were made with a plant stick, and seeds were put in by hand to a depth of 4 to 5 cm.

The field trial was terminated by manual removal and subsequent steaming of all cobs of the experimental plants. The remainders of the plants were mechanically chopped with a mowing machine.

The following observations were made. At the 2–3 leaf stage, the total number of germinated seeds was counted for each seedlot. As can be seen from Table 3, below, the percentage of germination varied between 63% and 100% with the exception of seedlot P4482, from which only 42% of the seeds germinated. Germination of seedlots of untransformed H99 and Pa91 plants varied between 25% and 75%.

At the 3–4 leaf stage, the phenotype of the transgenic neo gene was assayed as follows. In each plant, an incision up to the midvein was made in two leaves with a small pair of scissors. The incisions were then brushed with a piece of cotton wool drenched in an aqueous suspension of 4% kanamycin and 0.2% SDS. Some plants were treated with a suspension of 5% kanamycin and 0.1% SDS. A plant was scored as sensitive and as lacking an active neo gene when the newly formed leaves were yellow. A plant was scored as resistant and as having an active neo gene when the newly formed leaves were normal and showed no bleaching. Discoloration of the newly formed leaves was assessed about 10 days after the brushing. 5–8% of the tested plants had an intermediate phenotype as they could not be unambiguously scored as sensitive or resistant. This was probably due to variations in environmental conditions and/or developmental stages of the tested plants and a less than optimal kanamycin (and/or SDS) concentration.

In later analyses, the intermediate phenotypes were pooled with the sensitive plants. The proportions of kanamycin resistant plants versus kanamycin sensitive plants (including intermediate phenotypes) for each crossing or self was determined by a chi-square goodness of fit test (Snedecor and Cochran (1967) 'Statistical Methods', the Iowa State University Press, Ames, Iowa, U.S.A.) under the assumption of a one locus Mendelian segregation of the neo gene. The results are summarized in Table 3, below.

From the data in Table 3, it can be concluded that the introduced neo gene remained stable over three generations regardless of whether the progeny was obtained through selfing, backcrossing, or outcrossing to an unrelated line. The pattern of segregation was consistent with each original transformant having had only one active copy or multiple closely linked active copies of the neo gene and with the neo gene trait having had a normal Mendelian one-locus inheritance.

In all cases, the experimental plants appeared to be morphologically completely normal when compared to untransformed control plants.

TABLE 1

| | Cross | Seedlot |
|---|---|---|
| F1 | H99 x H99-M148-1 | P3166 |
| | Pa91 x H99-M148-1 | P3169 |
| | H99 x Pa91-M146-2 | P3162 |
| | Selfing of Pa91-M146-2 | P3173 (1) |
| F2 | P3169-024 x H99 | P3651 |
| | Selfing of P3166-002 | P3989 |
| | P3166-012 x H99 | P3983 |
| | P3166-018 x H99 | P3982 |
| | Selfing of P3173-003 | P3996 |
| | P3162-017 x H99 | P4004 |
| | P3162-008 x Pa91 | P4008 |
| F3 | H99 x (P3166-005 x H99)-001 | P4481 |
| | H99 x (P3162-004 x H99)-011 | P4483 |
| | Selfing of (Selfing of P3166-001)-003 | P4482 |
| | Pa91 x (P3169-028 x Pa91)-004 | P4310 |
| | H99 x (P3169-036 x H99)-003 | P4306 |

(1) not tested

TABLE 2

| Date | Activity | Quantity |
|---|---|---|
| March 29, 1991 | lime treatment of soil | 2000 kg/ha |
| May 23, 1991 | $NH_4NO_3$ treatment | 740 kg/ha |
| May 23, 1991 | superphosphate treatment | 833 kg/ha |
| May 23, 1991 | potassium sulphate | 120 kg/ha |
| May 27, 1991 | sowing of F1 and F2 seedlots | — |
| July 4, 1991 | Herbicide treatment: | |
| | Laddok | 4 l/ha |
| | paraffin oil | 105 l/ha |
| July 8, 1991 | Sowing of F3 seedlots | — |
| July 26, 1991 | Insecticide treatment: | |
| | Pyrimor | 0.265 kg/ha |
| | Ambush | 0.133 l/ha |
| October 10, 1991 | termination | — |

TABLE 3

| | Code | Emerg | % | T | R | I | S | ND | $X^2$ | Sign. |
|---|---|---|---|---|---|---|---|---|---|---|
| F1 | P3169 | 16/20 | 5 | 16 | 5 | 6 | 4 | 1 | 1.67 | n.s. |
| | P3166 | 79/100 | 4 | 79 | 36 | 0 | 35 | 8 | 0.01 | n.s. |
| | P3162 | 86/100 | 4 | 84 | 27 | 1 | 31 | 3 | 2.85 | n.s. |
| F2 | P3651 | 65/100 | 4 | 62 | 26 | 11 | 16 | 9 | 0.02 | n.s. |
| | P3989 | 91/100 | 4 | 83 | 66 | 1 | 10 | 5 | 4.71 | p <0.05 |
| | P3983 | 36/40 | 4 | 34 | 17 | 2 | 14 | 1 | 0.03 | n.s. |
| | P3982 | 51/60 | 4 | 42 | 20 | 4 | 17 | 1 | 0.02 | n.s. |
| | P3996 | 54/60 | 4 | 48 | 32 | 0 | 11 | 5 | 0.01 | n.s. |
| | P4004 | 92/100 | 4 | 86 | 38 | 11 | 31 | 6 | 0.20 | n.s. |
| | P4008 | 20/20 | 4 | 18 | 6 | 9 | 3 | 0 | 2.00 | n.s. |
| F3 | P4481 | 72/100 | 5 | 66 | 32 | 2 | 30 | 2 | 0 | n.s. |
| | P4483 | 63/100 | 5 | 47 | 22 | 2 | 23 | 0 | 0.19 | n.s. |
| | P4482 | 42/100 | 5 | 34 | 30 | 0 | 4 | 0 | 3.18 | n.s. |
| | P4310 | 84/100 | 5 | 82 | 50 | 7 | 24 | 1 | 4.46 | p <0.05 |
| | P4306 | 85/100 | 5 | 79 | 39 | 1 | 39 | 0 | 0.01 | n.s. |

Code=seedlot (see Table 1); Emerg=number of seedlings per number of sowed seeds; %=percentage of kanamycin in solution used in brushing assay; T=total number of plants tested; R=number of kanamycin resistant plants; I=number of intermediate phenotypes; S=number of kanamycin sensitive plants; ND=number of tested plants that were not scored because seedlings were stopped in growth and died; $X^2$=value of chi-square for segregation of R versus I+S (expected values in outcrossings are 50% R–50% I+S; expected values in selfings are 75% R–25% I+S under assumption of one locus segregation).

We claim:

1. A process for the stable integration of a DNA, said DNA comprising a gene that is functional in a cell of a corn plant in the nuclear genome of a corn plant, said process comprising:
   (a) providing a type I callus,
   (b) wounding and/or degrading said type I callus and transferring said DNA into the nuclear genome of a cell in said type I callus to generate a transformed cell, and,
   (c) regenerating a transformed corn plant from said transformed cell.

2. The process of claim 1, wherein said type I callus is wounded and/or degraded prior to transferring said DNA.

3. The process of claim 2, wherein said type I callus is wounded by being cut to callus pieces.

4. The process of claim 3, wherein said callus pieces have a maximum length of 0.5 to 2.5 mm.

5. The process of claim 4, wherein said callus pieces have a maximum length of 1 to 2 mm.

6. The process of claim 2, wherein said type I callus is wounded by treatment with an enzyme capable of degrading the cell walls of said callus for a period of time so as not to cause a complete disruption of the tissues.

7. The process of claim 6 in which said type I callus is treated with an enzyme capable of degrading the cell walls of said callus for a period of 1 to 10 minutes.

8. The process of claim 7, wherein said callus is treated with said enzyme for a period of 2 to 3 minutes.

9. The process of claim 1 or 3, in which said type I callus or said callus pieces are subjected to a period of plasmolysis prior to transferring said DNA.

10. The process of claim 1 in which said DNA is transferred into the nuclear genome of a cell in said type I callus by means of electroporation, direct gene transfer using polyethyleneglycol or bombardment with DNA coated microprojectiles.

11. The process of claim 1 in which said DNA is transferred into the nuclear genome of a cell in said type I callus by means of electroporation.

12. A process for the stable integration of a DNA, said DNA comprising a gene that is functional in a cell of a corn plant, into the nuclear genome of a corn plant, said process comprising:
    (a) obtaining an immature embryo from said corn plant,
    (b) wounding and/or degrading said immature embryo by treatment with an enzyme capable of degrading the cell walls of the cells of said immature embryo for a short period of time so as not to cause a complete disruption of the tissues and transferring said DNA into the nuclear genome of a cell in said immature embryo to generate a transformed cell, and,
    (c) regenerating a transformed corn plant from said transformed cell.

13. The process of claim 12 in which said immature embryo is treated with said enzyme for a period of 1 to 10 minutes.

14. The process of claim 12, in which the degraded immature embryo is subjected to a period of plasmolysis prior to transferring said DNA.

15. The process of claim 12, in which said DNA is transferred into the nuclear genome of a cell in the degraded immature embryos by means of electroporation, direct gene transfer using polyethyleneglycol or bombardment with DNA coated microprojectiles.

16. The process of claim 15, in which said DNA is transferred into the nuclear genome of a cell in said degraded immature embryo by means of electroporation.

17. The process of claim 12 in which the immature embryo has a maximum length of 0.5 to 1.5 mm.

18. The process of claim 1 in which said gene comprises the DNA encoding barnase under control of a stamen specific promoter of the TA29 gene of tobacco with a sequence within the DNA of SEQ ID No. 3 between nucleotide 1 and 545.

19. The process of claim 12 in which said gene comprises the DNA encoding barnase under control of a stamen specific promoter of the TA29 gene of tobacco with a sequence within the DNA of SEQ ID No. 3 between nucleotide 1 and 545.

20. The process of claim 1 in which said gene comprises a DNA coding for a phosphinothricin acetyltransferase or a neomycin phosphotransferase.

21. The process of claim 12 in which said gene comprises a DNA coding for a phosphinothricin acetyltransferase or a neomycin phosphotransferase.

22. The process of claim 1, wherein step (b) of said process is carried out by bombardment with DNA-coated microprojectiles.

23. The process of claim 3, in which said gene comprises the DNA encoding barnase under control of a stamen specific promoter of the TA29 gene of tobacco with a sequence within the DNA of SEQ ID No. 3 between nucleotide 1 and 545.

24. The process of claim 6, in which said gene comprises the DNA encoding barnase under control of a stamen specific promoter of the TA29 gene of tobacco with a sequence within the DNA of SEQ ID No. 3 between nucleotide 1 and 545.

25. The process of claim 3, in which said gene comprises a DNA coding for a phosphinothricin acetyltransferase or a neomycin phosphotransferase.

26. The process of claim 6, in which said gene comprises a DNA coding for a phosphinothricin acetyltransferase or a neomycin phosphotransferase.

27. The process of claim 2, in which said DNA is transferred into the nuclear genome of a cell in said type I callus by means of electroporation, direct gene transfer using polyethyleneglycol or bombardment with DNA coated microprojectiles.

28. The process of claim 3 in which said DNA is transferred into the nuclear genome of a cell in said type I callus by means of electroporation, direct gene transfer using polyethyleneglycol or bombardment with DNA coated microprojectiles.

29. The process of claim 1 in which said DNA is transferred into the nuclear genome of a cell in said type I callus by means of Agrobacterium-mediated DNA transfer.

30. The process of claim 2 in which said DNA is transferred into the nuclear genome of a cell in said type I callus by means of Agrobacterium-mediated transfer.

31. The process of claim 3 in which said DNA is transferred into the nuclear genome of a cell in said type I callus by means of Agrobacterium-mediated DNA transfer.

32. The process of claim 12 in which said DNA is transferred into the nuclear genome of a cell in the degraded immature embryo by means of Agrobacterium-mediated DNA transfer.

* * * * *

UNITED STATES PATENT AND TRADEMARK OFFICE
CERTIFICATE OF CORRECTION

PATENT NO. : 5,641,664             Page 1 of 2
DATED      : June 24, 1997
INVENTOR(S): D'HALLUIN et al.

It is certified that error appears in the above-identified patent and that said Letters Patent is hereby corrected as shown below:

In Claim 1, line 3, the word "in" should be replaced by --into--.

In Claim 17, line 2, the word "min" should be replaced by --mm--.

In Column 3, line 9, the word "hybridizes" should be replaced by --hybridize--.

In Column 3, line 32, the word "hybridizes" should be replaced by --hybridize--.

In Column 9, line 52, the word "Of" should be replaced by --of--.

In Column 9, line 66, the word "call" should be replaced by --cell--.

In Column 12, line 43, following the word "methods" please delete "7".

In Column 19, line 29, the sequence "AGCCATGGCG" should be replaced by --AGCCAGGCG--.

In Column 19, line 29, the sequence "TCGGTACCGC" should be replaced by --TCGGTCCGC--.

UNITED STATES PATENT AND TRADEMARK OFFICE
CERTIFICATE OF CORRECTION

PATENT NO. : 5,641,664
DATED : June 24, 1997
INVENTOR(S) : D'HALLUIN et al.

It is certified that error appears in the above-indentified patent and that said Letters Patent is hereby corrected as shown below:

In Column 22, line 11, the word "eletroporation" should be replaced by --electroporation--.

In Column 22, line 37, the word "gone" should be replaced by --gene--.

In Column 22, line 43, the word "HCL" should be replaced by --HCl--.

In Column 23, line 9, the word "pan" should be replaced by --part--.

In Column 24, line 46, the word "plnat" should be replaced by --plant--

Signed and Sealed this

Tenth Day of August, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 5399 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: plasmid pDE108

( i x ) FEATURE:
        ( A ) NAME/KEY: -
        ( B ) LOCATION: 1..451
        ( D ) OTHER INFORMATION: /label=pUC18
            / note= "pUC18 derived sequence"

( i x ) FEATURE:
        ( A ) NAME/KEY: -
        ( B ) LOCATION: 452..1284
        ( D ) OTHER INFORMATION: /label=35S3
            / note= "35S3 promoter sequence derived from
            Cauliflower mosaic virus isolate CabbB-JI"

( i x ) FEATURE:
        ( A ) NAME/KEY: -
        ( B ) LOCATION: 1285..2100
        ( D ) OTHER INFORMATION: /label=NPTII
            / note= "coding sequence of neomycine
            phosphotransferase gene"

( i x ) FEATURE:
        ( A ) NAME/KEY: -
        ( B ) LOCATION: 2101..3160
        ( D ) OTHER INFORMATION: /label=3'ocs
            / note= "3'regulatory sequence containing the
            polyadenylation site derived from the
            Agrobacterium T-DNA octopine synthase gene"

( i x ) FEATURE:
        ( A ) NAME/KEY: -
        ( B ) LOCATION: 3161..5399
        ( D ) OTHER INFORMATION: /label=pUC18
            / note= "pUC18 derived sequence"

( x i ) SEQUENCE DESCRIPTION: SEQ ID NO:1:

```
TCGCGCGTTT   CGGTGATGAC   GGTGAAAACC   TCTGACACAT   GCAGCTCCCG   GAGACGGTCA        60

CAGCTTGTCT   GTAAGCGGAT   GCCGGGAGCA   GACAAGCCCG   TCAGGGCGCG   TCAGCGGGTG       120

TTGGCGGGTG   TCGGGCTGG    CTTAACTATG   CGGCATCAGA   GCAGATTGTA   CTGAGAGTGC       180

ACCATATGCG   GTGTGAAATA   CCGCACAGAT   GCGTAAGGAG   AAAATACCGC   ATCAGGCGCC       240

ATTCGCCATT   CAGGCTGCGC   AACTGTTGGG   AAGGGCGATC   GGTGCGGGCC   TCTTCGCTAT       300

TACGCCAGCT   GGCGAAAGGG   GGATGTGCTG   CAAGGCGATT   AAGTTGGGTA   ACGCCAGGGT       360

TTTCCCAGTC   ACGACGTTGT   AAAACGACGG   CCAGTGAATT   CGAGCTCGGT   ACCCGGGGAT       420

CCTCTAGAGT   CGACCTGCAG   GCATGCAAGC   TCCTACGCAG   CAGGTCTCAT   CAAGACGATC       480

TACCCGAGTA   ACAATCTCCA   GGAGATCAAA   TACCTTCCCA   AGAAGGTTAA   AGATGCAGTC       540

AAAAGATTCA   GGACTAATTG   CATCAAGAAC   ACAGAGAAAG   ACATATTTCT   CAAGATCAGA       600
```

```
AGTACTATTC CAGTATGGAC GATTCAAGGC TTGCTTCATA AACCAAGGCA AGTAATAGAG    660
ATTGGAGTCT CTAAAAAGGT AGTTCCTACT GAATCTAAGG CCATGCATGG AGTCTAAGAT    720
TCAAATCGAG GATCTAACAG AACTCGCCGT GAAGACTGGC GAACAGTTCA TACAGAGTCT    780
TTTACGACTC AATGACAAGA AGAAAATCTT CGTCAACATG GTGGAGCACG ACACTCTGGT    840
CTACTCCAAA AATGTCAAAG ATACAGTCTC AGAAGACCAA AGGGCTATTG AGACTTTTCA    900
ACAAGGATA ATTTCGGGAA ACCTCCTCGG ATTCCATTGC CCAGCTATCT GTCACTTCAT    960
CGAAAGGACA GTAGAAAAGG AAGGTGGCTC CTACAAATGC CATCATTGCG ATAAAGGAAA   1020
GGCTATCATT CAAGATGCCT CTGCCGACAG TGGTCCCAAA GATGGACCCC CACCCACGAG   1080
GAGCATCGTG GAAAAGAAG ACGTTCCAAC CACGTCTTCA AAGCAAGTGG ATTGATGTGA    1140
CATCTCCACT GACGTAAGGG ATGACGCACA ATCCACTAT CCTTCGCAAG ACCCTTCCTC    1200
TATATAAGGA AGTTCATTTC ATTGGAGAG GACACGCTGA ATCACCAGT CTCTCTCTAT    1260
AAATCTATCT CTCTCTCTAT AACCATGGAT CCGGCCAAGC TAGCTTGGAT TGAACAAGAT   1320
GGATTGCACG CAGGTTCTCC GGCCGCTTGG GTGGAGAGGC TATTCGGCTA TGACTGGGCA   1380
CAACAGACAA TCGGCTGCTC TGATGCCGCC GTGTTCCGGC TGTCAGCGCA GGGGCGCCCG   1440
GTTCTTTTTG TCAAGACCGA CCTGTCCGGT GCCCTGAATG AACTGCAGGA CGAGGCAGCG   1500
CGGCTATCGT GGCTGGCCAC GACGGGCGTT CCTTGCGCAG CTGTGCTCGA CGTTGTCACT   1560
GAAGCGGGAA GGGACTGGCT GCTATTGGGC GAAGTGCCGG GCAGGATCT CCTGTCATCT   1620
CACCTTGCTC CTGCCGAGAA AGTATCCATC ATGGCTGATG CAATGCGGCG GCTGCATACG   1680
CTTGATCCGG CTACCTGCCC ATTCGACCAC CAAGCGAAAC ATCGCATCGA GCGAGCACGT   1740
ACTCGGATGG AAGCCGGTCT TGTCGATCAG GATGATCTGG ACGAAGAGCA TCAGGGGCTC   1800
GCGCCAGCCG AACTGTTCGC CAGGCTCAAG GCGCGCATGC CCGACGGCGA GGATCTCGTC   1860
GTGACCCATG GCGATGCCTG CTTGCCGAAT ATCATGGTGG AAAATGGCCG CTTTTCTGGA   1920
TTCATCGACT GTGGCCGGCT GGGTGTGGCG GACCGCTATC AGGACATAGC GTTGGCTACC   1980
CGTGATATTG CTGAAGAGCT TGGCGGCGAA TGGGCTGACC GCTTCCTCGT GCTTTACGGT   2040
ATCGCCGCTC CCGATTCGCA GCGCATCGCC TTCTATCGCC TTCTTGACGA GTTCTTCTGA   2100
GCGGGACTCT GGGGTTCGAA ATGACCGACC AAGCGACGCC CAACCTGCCA TCACGAGATT   2160
TCGATTCCAC CGCCGCCTTC TATGAAAGGT TGGGCTTCGG AATCGTTTTC CGGGACGCCG   2220
GCTGGATGAT CCTCCAGCGC GGGGATCTCA TGCTGGAGTT CTTCGCCCAC CCCCTGCTTT   2280
AATGAGATAT GCGAGACGCC TATGATCGCA TGATATTTGC TTTCAATTCT GTTGTGCACG   2340
TTGTAAAAAA CCTGAGCATG TGTAGCTCAG ATCCTTACCG CCGGTTTCGG TTCATTCTAA   2400
TGAATATATC ACCCGTTACT ATCGTATTTT TATGAATAAT ATTCTCCGTT CAATTTACTG   2460
ATTGTACCCT ACTACTTATA TGTACAATAT TAAAATGAAA ACAATATATT GTGCTGAATA   2520
GGTTTATAGC GACATCTATG ATAGAGCGCC ACAATAACAA ACAATTGCGT TTTATTATTA   2580
CAAATCCAAT TTTAAAAAAA GCGGCAGAAC CGGTCAAACC TAAAAGACTG ATTACATAAA   2640
TCTTATTCAA ATTTCAAAAG GCCCCAGGGG CTAGTATCTA CGACACACCG AGCGGCGAAC   2700
TAATAACGTT CACTGAAGGG AACTCCGGTT CCCGCCGGC GCGCATGGGT GAGATTCCTT    2760
GAAGTTGAGT ATTGGCCGTC CGCTCTACCG AAAGTTACGG GCACCATTCA ACCCGGTCCA   2820
GCACGGCGGC CGGGTAACCG ACTTGCTGCC CCGAGAATTA TGCAGCATTT TTTTGGTGTA   2880
TGTGGGCCCC AAATGAAGTG CAGGTCAAAC CTTGACAGTG ACGACAAATC GTTGGGCGGG   2940
TCCAGGGCGA ATTTTGCGAC AACATGTCGA GGCTCAGCAG GGGCTCGATC CCCTCGCGAG   3000
```

```
TTGGTTCAGC TGCTGCCTGA GGCTGGACGA CCTCGCGGAG TTCTACCGGC AGTGCAAATC    3060
CGTCGGCATC CAGGAAACCA GCAGCGGCTA TCCGCGCATC CATGCCCCCG AACTGCAGGA    3120
GTGGGGAGGC ACGATGGCCG CTTTGGTCGA CCTGCAGCCA AGCTTGGCGT AATCATGGTC    3180
ATAGCTGTTT CCTGTGTGAA ATTGTTATCC GCTCACAATT CCACACAACA TACGAGCCGG    3240
AAGCATAAAG TGTAAAGCCT GGGGTGCCTA ATGAGTGAGC TAACTCACAT TAATTGCGTT    3300
GCGCTCACTG CCCGCTTTCC AGTCGGGAAA CCTGTCGTGC CAGCTGCATT AATGAATCGG    3360
CCAACGCGCG GGAGAGGCG GTTTGCGTAT GGGCGCTCT TCCGCTTCCT CGCTCACTGA    3420
CTCGCTGCGC TCGGTCGTTC GGCTGCGGCG AGCGGTATCA GCTCACTCAA AGGCGGTAAT    3480
ACGGTTATCC ACAGAATCAG GGATAACGC AGGAAAGAAC ATGTGAGCAA AAGGCCAGCA    3540
AAAGGCCAGG AACCGTAAAA AGGCCGCGTT GCTGGCGTTT TTCCATAGGC TCCGCCCCCC    3600
TGACGAGCAT CACAAAAATC GACGCTCAAG TCAGAGGTGG CGAAACCCGA CAGGACTATA    3660
AAGATACCAG GCGTTTCCCC CTGGAAGCTC CCTCGTGCGC TCTCCTGTTC CGACCCTGCC    3720
GCTTACCGGA TACCTGTCCG CCTTTCTCCC TTCGGGAAGC GTGGCGCTTT CTCAATGCTC    3780
ACGCTGTAGG TATCTCAGTT CGGTGTAGGT CGTTCGCTCC AAGCTGGGCT GTGTGCACGA    3840
ACCCCCCGTT CAGCCCGACC GCTGCGCCTT ATCCGGTAAC TATCGTCTTG AGTCCAACCC    3900
GGTAAGACAC GACTTATCGC CACTGGCAGC AGCCACTGGT AACAGGATTA GCAGAGCGAG    3960
GTATGTAGGC GGTGCTACAG AGTTCTTGAA GTGGTGGCCT AACTACGGCT ACACTAGAAG    4020
GACAGTATTT GGTATCTGCG CTCTGCTGAA GCCAGTTACC TTCGGAAAAA GAGTTGGTAG    4080
CTCTTGATCC GGCAAACAAA CCACCGCTGG TAGCGGTGGT TTTTTGTTT GCAAGCAGCA    4140
GATTACGCGC AGAAAAAAAG GATCTCAAGA AGATCCTTTG ATCTTTTCTA CGGGGTCTGA    4200
CGCTCAGTGG AACGAAAACT CACGTTAAGG GATTTGGTC ATGAGATTAT CAAAAAGGAT    4260
CTTCACCTAG ATCCTTTTAA ATTAAAAATG AAGTTTTAAA TCAATCTAAA GTATATATGA    4320
GTAAACTTGG TCTGACAGTT ACCAATGCTT AATCAGTGAG GCACCTATCT CAGCGATCTG    4380
TCTATTTCGT TCATCCATAG TTGCCTGACT CCCCGTCGTG TAGATAACTA CGATACGGGA    4440
GGGCTTACCA TCTGGCCCCA GTGCTGCAAT GATACCGCGA GACCCACGCT CACCGGCTCC    4500
AGATTTATCA GCAATAAACC AGCCAGCCGG AAGGGCCGAG CGCAGAAGTG GTCCTGCAAC    4560
TTTATCCGCC TCCATCCAGT CTATTAATTG TTGCCGGGAA GCTAGAGTAA GTAGTTCGCC    4620
AGTTAATAGT TTGCGCAACG TTGTTGCCAT TGCTACAGGC ATCGTGGTGT CACGCTCGTC    4680
GTTTGGTATG GCTTCATTCA GCTCCGGTTC CCAACGATCA AGGCGAGTTA CATGATCCCC    4740
CATGTTGTGC AAAAAAGCGG TTAGCTCCTT CGGTCCTCCG ATCGTTGTCA GAAGTAAGTT    4800
GGCCGCAGTG TTATCACTCA TGGTTATGGC AGCACTGCAT AATTCTCTTA CTGTCATGCC    4860
ATCCGTAAGA TGCTTTTCTG TGACTGGTGA GTACTCAACC AAGTCATTCT GAGAATAGTG    4920
TATGCGGCGA CCGAGTTGCT CTTGCCCGGC GTCAATACGG GATAATACCG CGCCACATAG    4980
CAGAACTTTA AAAGTGCTCA TCATTGGAAA ACGTTCTTCG GGGCGAAAAC TCTCAAGGAT    5040
CTTACCGCTG TTGAGATCCA GTTCGATGTA ACCCACTCGT GCACCCAACT GATCTTCAGC    5100
ATCTTTTACT TTCACCAGCG TTTCTGGGTG AGCAAAAACA GGAAGGCAAA ATGCCGCAAA    5160
AAAGGGAATA AGGGCGACAC GGAAATGTTG AATACTCATA CTCTTCCTTT TTCAATATTA    5220
TTGAAGCATT TATCAGGGTT ATTGTCTCAT GAGCGGATAC ATATTTGAAT GTATTTAGAA    5280
AAATAAACAA ATAGGGGTTC CGCGCACATT TCCCCGAAAA GTGCCACCTG ACGTCTAAGA    5340
AACCATTATT ATCATGACAT TAACCTATAA AAATAGGCGT ATCACGAGGC CCTTTCGTC     5399
```

( 2 ) INFORMATION FOR SEQ ID NO:2:

( i ) SEQUENCE CHARACTERISTICS:
        ( A ) LENGTH: 1186 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: probe ( i x ) FEATURE:
        ( A ) NAME/KEY: -
        ( B ) LOCATION: 1..8
        ( D ) OTHER INFORMATION: /note= "sequence derived from
            tapetum specific promoter of Nicotiana tabacum"

( i x ) FEATURE:
        ( A ) NAME/KEY: -
        ( B ) LOCATION: 9..790
        ( D ) OTHER INFORMATION: /label=NPTII
            / note= "coding sequence of neomycine
            phosphotransferase gene"

( i x ) FEATURE:
        ( A ) NAME/KEY: -
        ( B ) LOCATION: 791..1186
        ( D ) OTHER INFORMATION: /label=3'g7
            / note= "3'regulatory sequence containing the
            polyadenylation site derived from Agrobacterium
            T-DNA gene 7"

( x i ) SEQUENCE DESCRIPTION: SEQ ID NO:2:

```
AAGCTTGGAT GGATTGCACG CAGGTTCTCC GGCCGCTTGG GTGGAGAGGC TATTCGGCTA      60
TGACTGGGCA CAACAGACAA TCGGCTGCTC TGATGCCGCC GTGTTCCGGC TGTCAGCGCA     120
GGGGCGCCCG GTTCTTTTTG TCAAGACCGA CCTGTCCGGT GCCCTGAATG AACTGCAGGA     180
CGAGGCAGCG CGGCTATCGT GGCTGGCCAC GACGGGCGTT CCTTGCGCAG CTGTGCTCGA     240
CGTTGTCACT GAAGCGGGAA GGGACTGGCT GCTATTGGGC GAAGTGCCGG GGCAGGATCT     300
CCTGTCATCT CACCTTGCTC CTGCCGAGAA AGTATCCATC ATGGCTGATG CAATGCGGCG     360
GCTGCATACG CTTGATCCGG CTACCTGCCC ATTCGACCAC CAAGCGAAAC ATCGCATCGA     420
GCGAGCACGT ACTCGGATGG AAGCCGGTCT TGTCGATCAG GATGATCTGG ACGAAGAGCA     480
TCAGGGGCTC GCGCCAGCCG AACTGTTCGC CAGGCTCAAG GCGCGCATGC CCGACGGCGA     540
GGATCTCGTC GTGACCCATG GCGATGCCTG CTTGCCGAAT ATCATGGTGG AAAATGGCCG     600
CTTTTCTGGA TTCATCGACT GTGGCCGGCT GGGTGTGGCG GACCGCTATC AGGACATAGC     660
GTTGGCTACC CGTGATATTG CTGAAGAGCT TGGCGGCGAA TGGGCTGACC GCTTCCTCGT     720
GCTTTACGGT ATCGCCGCTC CCGATTCGCA GCGCATCGCC TTCTATCGCC TTCTTGACGA     780
GTTCTTCTGA GCGGGACTCT GGGGTTCGAA ATGACCGACC AAGCGACGCC CAACCTGCCA     840
TCACGAGATT TCGATTCCAC CGCCGCCTTC TATGAAAGGT TGGGCTTCGG AATCGTTTTC     900
CGGGACGCCG GCTGGATGAT CCTCCAGCGC GGGGATCTCA TGCTGGAGTT CTTCGCCCAC     960
CCCGATCCAT GAGCTAAGCT AGCTATATCA TCAATTTATG TATTACACAT AATATCGCAC    1020
TCAGTCTTTC ATCTACGGCA ATGTACCAGC TGATATAATC AGTTATTGAA ATATTTCTGA    1080
ATTTAAACTT GCATCAATAA ATTTATGTTT TTGCTTGGAC TATAATACCT GACTTGTTAT    1140
```

TTTATCAATA AATATTTAAA CTATATTTCT TTCAAGATGG GAATTC                                1186

(2) INFORMATION FOR SEQ ID NO:3:

(i) SEQUENCE CHARACTERISTICS:
        (A) LENGTH: 1287 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: fragment of pTTM8

(ix) FEATURE:
        (A) NAME/KEY: -
        (B) LOCATION: 1..545
        (D) OTHER INFORMATION: /label=PTA29
            / note= "Promoter from the TA29 gene of Nicotiana
            tabacum"

(ix) FEATURE:
        (A) NAME/KEY: -
        (B) LOCATION: 546..881
        (D) OTHER INFORMATION: /label=barnase
            / note= "coding sequence of barnase gene"

(ix) FEATURE:
        (A) NAME/KEY: -
        (B) LOCATION: 882..1287
        (D) OTHER INFORMATION: /label=3'nos
            / note= "3' regulatory sequence containing the
            polyadenylation site derived from Agrobacterium
            T-DNA nopaline synthase gene "

(xi) SEQUENCE DESCRIPTION: SEQ ID NO:3:

ATCTAGCTAA GTATAACTGG ATAATTTGCA TTAACAGATT GAATATAGTG CCAAACAAGA          60

AGGGACAATT GACTTGTCAC TTTATGAAAG ATGATTCAAA CATGATTTTT TATGTACTAA         120

TATATACATC CTACTCGAAT TAAAGCGACA TAGGCTCGAA GTATGCACAT TTAGCAATGT         180

AAATTAAATC AGTTTTTGAA TCAAGCTAAA AGCAGACTTG CATAAGGTGG GTGGCTGGAC         240

TAGAATAAAC ATCTTCTCTA GCACAGCTTC ATAATGTAAT TTCCATAACT GAAATCAGGG         300

TGAGACAAAA TTTTGGTACT TTTTCCTCAC ACTAAGTCCA TGTTTGCAAC AAATTAATAC         360

ATGAAACCTT AATGTTACCC TCAGATTAGC CTGCTACTCC CCATTTTCCT CGAAATGCTC         420

CAACAAAAGT TAGTTTTGCA AGTTGTTGTG TATGTCTTGT GCTCTATATA TGCCCTTGTG         480

GTGCAAGTGT AACAGTACAA CATCATCACT CAAATCAAAG TTTTTACTTA AAGAAATTAG         540

CTACCATGGT ACCGGTTATC AACACGTTTG ACGGGGTTGC GGATTATCTT CAGACATATC         600

ATAAGCTACC TGATAATTAC ATTACAAAAT CAGAAGCACA AGCCCTCGGC TGGGTGGCAT         660

CAAAAGGGAA CCTTGCAGAC GTCGCTCCGG GGAAAAGCAT CGGCGGAGAC ATCTTCTCAA         720

ACAGGGAAGG CAAACTCCCG GGCAAAAGCG GACGAACATG GCGTGAAGCG GATATTAACT         780

ATACATCAGG CTTCAGAAAT TCAGACCGGA TTCTTTACTC AAGCGACTGG CTGATTTACA         840

AAACAACGGA CCATTATCAG ACCTTTACAA AAATCAGATA ACGAAAAAAA CGGCTTCCTG         900

CGGAGGCCGT TTTTTCAGC TTTACATAAA GTGTGTAATA AATTTTTCTT CAAACTCTGA          960

TCGGTCAATT TCACTTTCCG GNNNNCTCTA GAGGATCCGA AGCAGATCGT TCAAACATTT        1020

GGCAATAAAG TTTCTTAAGA TTGAATCCTG TTGCCGGTCT TGCGATGATT ATCATATAAT        1080

TTCTGTTGAA TTACGTTAAG CATGTAATAA TTAACATGTA ATGCATGACG TTATTTATGA        1140

| | | | | | | |
|---|---|---|---|---|---|---|
| GATGGGTTTT | TATGATTAGA | GTCCCGCAAT | TATACATTTA | ATACGCGATA | GAAAACAAAA | 1200 |
| TATAGCGCGC | AAACTAGGAT | AAATTATCGC | GCGCGGTGTC | ATCTATGTTA | CTAGATCGGG | 1260 |
| AAGATCCCCG | GGTACCGAGC | TCGAATT | | | | 1287 |

( 2 ) INFORMATION FOR SEQ ID NO:4:

( i ) SEQUENCE CHARACTERISTICS:
        ( A ) LENGTH: 4883 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: plasmid pDE110

( i x ) FEATURE:
        ( A ) NAME/KEY: -
        ( B ) LOCATION: 1..395
        ( D ) OTHER INFORMATION: /label=pUC18
            / note= "pUC18 derived sequence"

( i x ) FEATURE:
        ( A ) NAME/KEY: -
        ( B ) LOCATION: 396..1779
        ( D ) OTHER INFORMATION: /label=35S3
            / note= "35S3 promoter sequence derived from
            Cauliflower mosaic virus isolate CabbB-JI"

( i x ) FEATURE:
        ( A ) NAME/KEY: -
        ( B ) LOCATION: 1780..2331
        ( D ) OTHER INFORMATION: /label=bar
            / note= "coding sequence of phosphinothricin
            acetyltransferase gene"

( i x ) FEATURE:
        ( A ) NAME/KEY: -
        ( B ) LOCATION: 2332..2619
        ( D ) OTHER INFORMATION: /label=3'nos
            / note= "3'regulatory sequence containing the
            polyadenylation site derived from Agrobacterium
            T-DNA nopaline synthase gene"

( i x ) FEATURE:
        ( A ) NAME/KEY: -
        ( B ) LOCATION: 2620..4883
        ( D ) OTHER INFORMATION: /label=pUC18
            / note= "pUC18 derived sequence"

( x i ) SEQUENCE DESCRIPTION: SEQ ID NO:4:

| | | | | | | |
|---|---|---|---|---|---|---|
| TCGCGCGTTT | CGGTGATGAC | GGTGAAAACC | TCTGACACAT | GCAGCTCCCG | GAGACGGTCA | 60 |
| CAGCTTGTCT | GTAAGCGGAT | GCCGGGAGCA | GACAAGCCCG | TCAGGGCGCG | TCAGCGGGTG | 120 |
| TTGGCGGGTG | TCGGGCTGG | CTTAACTATG | CGGCATCAGA | GCAGATTGTA | CTGAGAGTGC | 180 |
| ACCATATGCG | GTGTGAAATA | CCGCACAGAT | GCGTAAGGAG | AAAATACCGC | ATCAGGCGCC | 240 |
| ATTCGCCATT | CAGGCTGCGC | AACTGTTGGG | AAGGGCGATC | GGTGCGGGCC | TCTTCGCTAT | 300 |
| TACGCCAGCT | GGCGAAAGGG | GGATGTGCTG | CAAGGCGATT | AAGTTGGGTA | ACGCCAGGGT | 360 |
| TTTCCCAGTC | ACGACGTTGT | AAAACGACGG | CCAGTGAATT | CCAATCCCAC | CAAAACCTGA | 420 |
| ACCTAGCAGT | TCAGTTGCTC | CTCTCAGAGA | CGAATCGGGT | ATTCAACACC | CTCATACCAA | 480 |
| CTACTACGTC | GTGTATAACG | GACCTCATGC | CGGTATATAC | GATGACTGGG | GTTGTACAAA | 540 |
| GGCAGCAACA | AACGGTGTTC | CCGGAGTTGC | GCATAAGAAG | TTTGCCACTA | TTACAGAGGC | 600 |

```
AAGAGCAGCA  GCTGACGCGT  ATACAACAAG  TCAGCAAACA  GATAGGTTGA  ACTTCATCCC    660

CAAAGGAGAA  GCTCAACTCA  AGCCCAAGAG  CTTTGCGAAG  GCCCTAACAA  GCCCACCAAA    720

GCAAAAAGCC  CACTGCTCAC  GCTAGGAACC  AAAAGGCCCA  GCAGTGATCC  AGCCCCAAAA    780

GAGATCTCCT  TTGCCCCGGA  GATTACAATG  GACGATTTCC  TCTATCTTTA  CGATCTAGGA    840

AGGAAGTTCG  AAGGTGAAGG  TGACGACACT  ATGTTCACCA  CTGATAATGA  AAGGTTAGC     900

CTCTTCAATT  TCAGAAAGAA  TGCTGACCCA  CAGATGGTTA  GAGAGGCCTA  CGCAGCAGGT    960

CTCATCAAGA  CGATCTACCC  GAGTAACAAT  CTCCAGGAGA  TCAAATACCT  TCCCAAGAAG   1020

GTTAAAGATG  CAGTCAAAAG  ATTCAGGACT  AATTGCATCA  AGAACACAGA  GAAAGACATA   1080

TTTCTCAAGA  TCAGAAGTAC  TATTCCAGTA  TGGACGATTC  AAGGCTTGCT  TCATAAACCA   1140

AGGCAAGTAA  TAGAGATTGG  AGTCTCTAAA  AAGGTAGTTC  CTACTGAATC  TAAGGCCATG   1200

CATGGAGTCT  AAGATTCAAA  TCGAGGATCT  AACAGAACTC  GCCGTGAAGA  CTGGCGAACA   1260

GTTCATACAG  AGTCTTTTAC  GACTCAATGA  CAAGAAGAAA  ATCTTCGTCA  ACATGGTGGA   1320

GCACGACACT  CTGGTCTACT  CCAAAAATGT  CAAAGATACA  GTCTCAGAAG  ACCAAAGGGC   1380

TATTGAGACT  TTTCAACAAA  GGATAATTTC  GGGAAACCTC  CTCGGATTCC  ATTGCCAGC    1440

TATCTGTCAC  TTCATCGAAA  GGACAGTAGA  AAAGGAAGGT  GGCTCCTACA  AATGCCATCA   1500

TTGCGATAAA  GGAAAGGCTA  TCATTCAAGA  TGCCTCTGCC  GACAGTGGTC  CCAAAGATGG   1560

ACCCCCACCC  ACGAGGAGCA  TCGTGGAAAA  AGAAGACGTT  CCAACCACGT  CTTCAAAGCA   1620

AGTGGATTGA  TGTGACATCT  CCACTGACGT  AAGGGATGAC  GCACAATCCC  ACTATCCTTC   1680

GCAAGACCCT  TCCTCTATAT  AAGGAAGTTC  ATTTCATTTG  GAGAGGACAC  GCTGAAATCA   1740

CCAGTCTCTC  TCTATAAATC  TATCTCTCTC  TCTATAACCA  TGGACCCAGA  ACGACGCCCG   1800

GCCGACATCC  GCCGTGCCAC  CGAGGCGGAC  ATGCCGGCGG  TCTGCACCAT  CGTCAACCAC   1860

TACATCGAGA  CAAGCACGGT  CAACTTCCGT  ACCGAGCCGC  AGGAACCGCA  GGAGTGGACG   1920

GACGACCTCG  TCCGTCTGCG  GGAGCGCTAT  CCCTGGCTCG  TCGCCGAGGT  GGACGGCGAG   1980

GTCGCCGGCA  TCGCCTACGC  GGGCCCCTGG  AAGGCACGCA  ACGCCTACGA  CTGGACGGCC   2040

GAGTCGACCG  TGTACGTCTC  CCCCCGCCAC  CAGCGGACGG  GACTGGGCTC  CACGCTCTAC   2100

ACCCACCTGC  TGAAGTCCCT  GGAGGCACAG  GGCTTCAAGA  GCGTGGTCGC  TGTCATCGGG   2160

CTGCCCAACG  ACCCGAGCGT  GCGCATGCAC  GAGGCGCTCG  GATATGCCCC  CGCGGCATG    2220

CTGCGGGCGG  CCGGCTTCAA  GCACGGGAAC  TGGCATGACG  TGGGTTTCTG  GCAGCTGGAC   2280

TTCAGCCTGC  CGGTACCGCC  CCGTCCGGTC  CTGCCCGTCA  CCGAGATCTG  ATCTCACGCG   2340

TCTAGGATCC  GAAGCAGATC  GTTCAAACAT  TTGGCAATAA  AGTTTCTTAA  GATTGAATCC   2400

TGTTGCCGGT  CTTGCGATGA  TTATCATATA  ATTTCTGTTG  AATTACGTTA  AGCATGTAAT   2460

AATTAACATG  TAATGCATGA  CGTTATTTAT  GAGATGGGTT  TTTATGATTA  GAGTCCCGCA   2520

ATTATACATT  TAATACGCGA  TAGAAAACAA  AATATAGCGC  GCAAACTAGG  ATAAATTATC   2580

GCGCGCGGTG  TCATCTATGT  TACTAGATCG  GGAAGATCCT  CTAGAGTCGA  CCTGCAGGCA   2640

TGCAAGCTTG  GCGTAATCAT  GGTCATAGCT  GTTTCCTGTG  TGAAATTGTT  ATCCGCTCAC   2700

AATTCCACAC  AACATACGAG  CCGGAAGCAT  AAAGTGTAAA  GCCTGGGGTG  CCTAATGAGT   2760

GAGCTAACTC  ACATTAATTG  CGTTGCGCTC  ACTGCCCGCT  TCCAGTCGG   GAAACCTGTC   2820

GTGCCAGCTG  CATTAATGAA  TCGGCCAACG  CGCGGGGAGA  GGCGGTTTGC  GTATTGGGCG   2880

CTCTTCCGCT  TCCTCGCTCA  CTGACTCGCT  GCGCTCGGTC  GTTCGGCTGC  GGCGAGCGGT   2940

ATCAGCTCAC  TCAAAGGCGG  TAATACGGTT  ATCCACAGAA  TCAGGGGATA  ACGCAGGAAA   3000
```

-continued

```
GAACATGTGA GCAAAAGGCC AGCAAAAGGC CAGGAACCGT AAAAAGGCCG CGTTGCTGGC    3060
GTTTTTCCAT AGGCTCCGCC CCCCTGACGA GCATCACAAA AATCGACGCT CAAGTCAGAG    3120
GTGGCGAAAC CCGACAGGAC TATAAAGATA CCAGGCGTTT CCCCCTGGAA GCTCCCTCGT    3180
GCGCTCTCCT GTTCCGACCC TGCCGCTTAC CGGATACCTG TCCGCCTTTC TCCCTTCGGG    3240
AAGCGTGGCG CTTTCTCAAT GCTCACGCTG TAGGTATCTC AGTTCGGTGT AGGTCGTTCG    3300
CTCCAAGCTG GGCTGTGTGC ACGAACCCCC CGTTCAGCCC GACCGCTGCG CCTTATCCGG    3360
TAACTATCGT CTTGAGTCCA ACCCGGTAAG ACACGACTTA TCGCCACTGG CAGCAGCCAC    3420
TGGTAACAGG ATTAGCAGAG CGAGGTATGT AGGCGGTGCT ACAGAGTTCT TGAAGTGGTG    3480
GCCTAACTAC GGCTACACTA GAAGGACAGT ATTTGGTATC TGCGCTCTGC TGAAGCCAGT    3540
TACCTTCGGA AAAGAGTTG GTAGCTCTTG ATCCGGCAAA CAAACCACCG CTGGTAGCGG    3600
TGGTTTTTTT GTTTGCAAGC AGCAGATTAC GCGCAGAAAA AAAGGATCTC AAGAAGATCC    3660
TTTGATCTTT TCTACGGGGT CTGACGCTCA GTGGAACGAA AACTCACGTT AAGGGATTTT    3720
GGTCATGAGA TTATCAAAAA GGATCTTCAC CTAGATCCTT TTAAATTAAA AATGAAGTTT    3780
TAAATCAATC TAAAGTATAT ATGAGTAAAC TTGGTCTGAC AGTTACCAAT GCTTAATCAG    3840
TGAGGCACCT ATCTCAGCGA TCTGTCTATT TCGTTCATCC ATAGTTGCCT GACTCCCCGT    3900
CGTGTAGATA ACTACGATAC GGGAGGGCTT ACCATCGGC CCCAGTGCTG CAATGATACC    3960
GCGAGACCCA CGCTCACCGG CTCCAGATTT ATCAGCAATA AACCAGCCAG CCGGAAGGGC    4020
CGAGCGCAGA AGTGGTCCTG CAACTTTATC CGCCTCCATC CAGTCTATTA ATTGTTGCCG    4080
GGAAGCTAGA GTAAGTAGTT CGCCAGTTAA TAGTTTGCGC AACGTTGTTG CCATTGCTAC    4140
AGGCATCGTG GTGTCACGCT CGTCGTTTGG TATGGCTTCA TTCAGCTCCG GTTCCCAACG    4200
ATCAAGGCGA GTTACATGAT CCCCCATGTT GTGCAAAAAA GCGGTTAGCT CCTTCGGTCC    4260
TCCGATCGTT GTCAGAAGTA AGTTGGCCGC AGTGTTATCA CTCATGGTTA TGGCAGCACT    4320
GCATAATTCT CTTACTGTCA TGCCATCCGT AAGATGCTTT TCTGTGACTG GTGAGTACTC    4380
AACCAAGTCA TTCTGAGAAT AGTGTATGCG GCGACCGAGT TGCTCTTGCC CGGCGTCAAT    4440
ACGGGATAAT ACCGCGCCAC ATAGCAGAAC TTTAAAAGTG CTCATCATTG GAAAACGTTC    4500
TTCGGGGCGA AAACTCTCAA GGATCTTACC GCTGTTGAGA TCCAGTTCGA TGTAACCCAC    4560
TCGTGCACCC AACTGATCTT CAGCATCTTT TACTTTCACC AGCGTTTCTG GGTGAGCAAA    4620
AACAGGAAGG CAAAATGCCG CAAAAAAGGG AATAAGGGCG ACACGGAAAT GTTGAATACT    4680
CATACTCTTC CTTTTTCAAT ATTATTGAAG CATTTATCAG GGTTATTGTC TCATGAGCGG    4740
ATACATATTT GAATGTATTT AGAAAAATAA ACAAATAGGG GTTCCGCGCA CATTTCCCCG    4800
AAAAGTGCCA CCTGACGTCT AAGAAACCAT TATTATCATG ACATTAACCT ATAAAAATAG    4860
GCGTATCACG AGGCCCTTTC GTC                                            4883
```

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

```
AGCCATGGCG                                                              10
```